US010039722B2

(12) United States Patent
Miller

(10) Patent No.: US 10,039,722 B2
(45) Date of Patent: Aug. 7, 2018

(54) TREATMENT OF OXIDATIVE STRESS DISORDERS INCLUDING CONTRAST NEPHROPATHY, RADIATION DAMAGE AND DISRUPTIONS IN THE FUNCTION OF RED CELLS

(75) Inventor: Guy M. Miller, Monte Sereno, CA (US)

(73) Assignee: BIOELECTRON TECHNOLOGY CORPORATION, Mountain View, CA (US)

( * ) Notice: Subject to any disclaimer, the term of this patent is extended or adjusted under 35 U.S.C. 154(b) by 380 days.

(21) Appl. No.: 13/123,496

(22) PCT Filed: Oct. 13, 2009

(86) PCT No.: PCT/US2009/060489
§ 371 (c)(1),
(2), (4) Date: May 26, 2011

(87) PCT Pub. No.: WO2010/045220
PCT Pub. Date: Apr. 22, 2010

(65) Prior Publication Data
US 2011/0269776 A1 Nov. 3, 2011

Related U.S. Application Data

(60) Provisional application No. 61/196,136, filed on Oct. 14, 2008.

(51) Int. Cl.
A61K 31/122 (2006.01)
A61K 31/00 (2006.01)
A61K 31/025 (2006.01)

(52) U.S. Cl.
CPC ............ *A61K 31/00* (2013.01); *A61K 31/025* (2013.01); *A61K 31/122* (2013.01)

(58) Field of Classification Search
CPC .................................................. A61K 31/122
See application file for complete search history.

(56) References Cited

U.S. PATENT DOCUMENTS

| 5,376,361 | A | * | 12/1994 | Perricone ..................... 424/59 |
| 5,801,159 | A | | 9/1998 | Miller et al. |
| 5,874,461 | A | | 2/1999 | De Chaffoy de Courcelles et al. |
| 6,056,965 | A | | 5/2000 | Yadan et al. |
| 6,232,060 | B1 | | 5/2001 | Miller et al. |
| 6,426,362 | B1 | | 7/2002 | Miller et al. |
| 6,528,042 | B1 | | 3/2003 | Brown et al. |
| 6,608,196 | B2 | | 8/2003 | Wang et al. |
| 6,653,346 | B1 | | 11/2003 | Wang et al. |
| 7,034,054 | B2 | | 4/2006 | Miller et al. |
| 7,078,541 | B2 | | 7/2006 | Boddupalli et al. |
| 7,119,117 | B2 | | 10/2006 | Beinlich et al. |
| 7,393,662 | B2 | | 7/2008 | Heavner et al. |
| 7,432,305 | B2 | | 10/2008 | Miller et al. |
| 7,470,798 | B2 | | 12/2008 | Wang et al. |
| 7,491,312 | B2 | | 2/2009 | Gilat et al. |
| 7,514,461 | B2 | | 4/2009 | Wang et al. |
| 7,718,176 | B2 | | 5/2010 | Heavner et al. |
| 7,875,607 | B2 | | 1/2011 | Wang et al. |
| 7,968,746 | B2 | | 6/2011 | Jankowski et al. |
| 8,044,097 | B2 | | 10/2011 | Wang et al. |
| 8,106,223 | B2 | | 1/2012 | Wesson et al. |
| 8,314,153 | B2 | | 11/2012 | Miller et al. |
| 8,519,001 | B2 | | 8/2013 | Jankowski et al. |
| 8,575,369 | B2 | | 11/2013 | Wesson et al. |
| 2002/0132845 | A1 | | 9/2002 | Miller et al. |
| 2003/0022818 | A1 | | 1/2003 | Miller et al. |
| 2003/0050297 | A1 | | 3/2003 | Crapo et al. |
| 2003/0103954 | A1 | | 6/2003 | Rosenbloom |
| 2003/0144219 | A1 | | 7/2003 | Phinney et al. |
| 2003/0158213 | A1 | | 8/2003 | Freeman et al. |
| 2005/0065099 | A1 | | 3/2005 | Walkinshaw et al. |
| 2005/0239807 | A1 | | 10/2005 | Stamler et al. |
| 2006/0247306 | A1 | * | 11/2006 | Kumar et al. ................. 514/458 |
| 2006/0281809 | A1 | | 12/2006 | Miller et al. |
| 2007/0072943 | A1 | | 3/2007 | Miller et al. |
| 2007/0225261 | A1 | | 9/2007 | Miller et al. |
| 2008/0214653 | A1 | | 9/2008 | Zicker et al. |
| 2009/0118257 | A1 | | 5/2009 | Jankowski et al. |
| 2009/0162890 | A1 | | 6/2009 | Gilat et al. |

(Continued)

FOREIGN PATENT DOCUMENTS

EP 1 074 254 A2 2/2001
EP 1 074 254 A3 2/2001

(Continued)

OTHER PUBLICATIONS

Ogawa et al. Jul. 2008, Free Radical Research, vol. 42(7), pp. 674-687.*
Hopewell 1990, Int. J. Radiation Biology, vol. 57, No. 4, pp. 751-773.*
Berndorfer-Kraszner et al. 1971, Elelmezesi Ipar, vol. 25, No. 11, pp. 339-345.*
Berndorfer-Kraszner et al. 1971, English translation.*
Adler, V. et al. (Mar. 1, 1999). "Regulation of JNK Signaling by GSTp," *The EMBO Journal* 18(5):1321-1334.
Adler, V. et al. (Nov. 1, 1999). "Role of Redox Potential and Reactive Oxygen Species in Stress Signaling," *Oncogene* 18(45):6104-6111.
Carroll. F.I. et al. (Sep. 1990). "S-[2-[(2'-Carbamoylethyl)amino]ethyl] Phosphorothioate and Related Compounds as Potential Antiradiation Agents," *Journal of Medicinal Chemistry* 33(9):2501-2508.

(Continued)

*Primary Examiner* — Kara R McMillian
(74) *Attorney, Agent, or Firm* — Squire Patton Boggs (US) LLP

(57) ABSTRACT

Methods of treating or suppressing oxidative stress diseases and symptoms related to oxidative stress affecting normal electron flow in the cells or caused by reactive oxygen species with redox-active therapeutics. Use of redox-active therapeutics for the reduction, suppression or treatment of oxidative stress induced by chemical agents such as contrast agents and other nephrotoxic agents, by radiation exposure, and by disruptions in the transport of oxygen to tissues, is disclosed.

13 Claims, No Drawings

(56) References Cited

U.S. PATENT DOCUMENTS

| | | |
|---|---|---|
| 2009/0163529 A1 | 6/2009 | Gilat et al. |
| 2009/0291092 A1 | 11/2009 | Miller et al. |
| 2010/0010100 A1 | 1/2010 | Hinman et al. |
| 2010/0029784 A1 | 2/2010 | Hinman et al. |
| 2010/0056429 A1 | 3/2010 | Miller et al. |
| 2010/0222436 A1 | 9/2010 | Miller et al. |
| 2010/0249032 A1 | 9/2010 | Heavner et al. |
| 2010/0266591 A1 | 10/2010 | Bugelski et al. |
| 2010/0273892 A1 | 10/2010 | Miller et al. |
| 2010/0273894 A1 | 10/2010 | Miller |
| 2011/0046156 A1 | 2/2011 | Miller |
| 2011/0046219 A1 | 2/2011 | Hinman et al. |
| 2011/0124679 A1 | 5/2011 | Hinman et al. |
| 2011/0142834 A1 | 6/2011 | Miller |
| 2011/0172312 A1 | 7/2011 | Miller et al. |
| 2011/0207828 A1 | 8/2011 | Miller et al. |
| 2011/0218208 A1 | 9/2011 | Hinman et al. |
| 2012/0088783 A1 | 4/2012 | Wang et al. |
| 2012/0101169 A1 | 4/2012 | Hawi |
| 2012/0122969 A1 | 5/2012 | Miller |
| 2012/0136048 A1 | 5/2012 | Miller et al. |
| 2012/0295985 A1 | 11/2012 | Miller et al. |
| 2013/0053450 A1 | 2/2013 | Miller et al. |
| 2013/0109759 A1 | 5/2013 | Miller |
| 2013/0116336 A1 | 5/2013 | Shrader |
| 2013/0267538 A1 | 10/2013 | Walkinshaw et al. |
| 2013/0289034 A1 | 10/2013 | Jankowski et al. |
| 2013/0345312 A1 | 12/2013 | Jankowski et al. |
| 2014/0031432 A1 | 1/2014 | Jankowski et al. |
| 2014/0031433 A1 | 1/2014 | Miller et al. |
| 2014/0039065 A1 | 2/2014 | Miller |

FOREIGN PATENT DOCUMENTS

| | | |
|---|---|---|
| GB | 2 269 748 A | 2/1994 |
| WO | WO-98/33495 A1 | 8/1998 |
| WO | WO-00/78296 A2 | 12/2000 |
| WO | WO-00/78296 A3 | 12/2000 |
| WO | WO-02/47680 A2 | 6/2002 |
| WO | WO-02/47680 A3 | 6/2002 |
| WO | WO-02/47680 A9 | 6/2002 |
| WO | WO-03/064403 A1 | 8/2003 |
| WO | WO-2007/046729 A1 | 4/2007 |
| WO | WO-2008/023064 A2 | 2/2008 |
| WO | WO-2008/023064 A3 | 2/2008 |
| WO | WO-2008/065891 A1 | 6/2008 |
| WO | WO-2009/089224 A1 | 7/2009 |
| WO | WO-2009/111576 A2 | 9/2009 |
| WO | WO-2009/111576 A3 | 9/2009 |
| WO | WO-2009/126866 A2 | 10/2009 |
| WO | WO-2009/126866 A3 | 10/2009 |
| WO | WO-2009/158348 A1 | 12/2009 |
| WO | WO-2011/041452 A2 | 4/2011 |
| WO | WO-2011/113018 A1 | 9/2011 |
| WO | WO-2012/019029 A2 | 2/2012 |
| WO | WO-2012/019029 A3 | 2/2012 |
| WO | WO-2012/019032 A1 | 2/2012 |
| WO | WO-2012/154613 A1 | 11/2012 |
| WO | WO-2012/170773 A1 | 12/2012 |
| WO | WO-2012/174286 A1 | 12/2012 |
| WO | WO-2013/006736 A1 | 1/2013 |
| WO | WO-2013/006737 A1 | 1/2013 |
| WO | WO-2013/013078 A1 | 1/2013 |

OTHER PUBLICATIONS

Diomedi-Camassei, F. et al. (Oct. 2007). "COQ2 Nephropathy: A Newly Described Inherited Mitochondriopathy with Primary Renal Involvement," *Journal of the American Society of Nephrology* 18(10):2773-2780.

Fouda, A-M.M. et al. (2008). "Thymoquinone Ameliorates Renal Oxidative Damage and Proliferative Response Induced by Mercuric Chloride in Rats," *Basic & Clinical Pharmacology & Toxicology* 103(2):109-118.

Garofalo, A.S. et al. (2007). "Reactive Oxygen Species Independent Cytotoxicity Induced by Radiocontrast Agents in Tubular Cells (LLC-PK1 and MDCK)," *Renal Failure* 29:121-131.

Haller, C. et al. (Mar. 2004). "The Cytotoxicity of Iodinated Radiocontrast Agents on Renal Cells In Vitro," *Investigative Radiology* 39(3):149-154.

Heyman, S.N. et al. (Nov. 1999). "Pathophysiology of Radiocontrast Nephropathy: A Role for Medullary Hypoxia," *Investigative Radiology* 34(11):685-691.

Kalpravidh, R.W. et al. (2005). "Effect of CoEnzyme $Q_{10}$ as an Antioxidant in γ-thalassemia/Hb E Patients," *BioFactors* 25:225-234.

Kawai, Y. et al. (Mar. 31, 2008). "Cisplatin-induced Renal Injury in $LLC-PK_1$ Cells," *Proceedings of the $6^{th}$ World Congress on Alternatives & Animal Use in the Life Sciences*, Tokyo, Japan, Aug. 21-25, 2007, *Alternatives to Animal Testing and Experimentation Journal* 14(Special Issue):453-456.

Lee, P.I. (1992). "Diffusion-Controlled Matrix Systems," Chapter 3 in *Treatise on Controlled Dug Delivery*, Kydonieus, A. ed., Marcel Dekker, Inc., New York, NY, pp. 155-197.

NIH Reporter, Project Information No. Y1AI9431-1-0-1, last updated Oct. 23, 2009, "Countermeasures Against Radiological and Nuclear Attack," located at <http://projectreporter.nih.gov/reporter.cfm>, 1 page.

Pike, B.L. et al. (Aug. 1970). "Human Bone Marrow Colony Growth in Agar-gel," *Journal of Cellular Physiology* 76(1):77-84.

Ramesh, N. et al. (Jun. 2006). "Reno-Protective Effect of N-Acetyl Cysteine in Patients with Impaired Renal Function Undergoing Coronary Angiography and Interventions," *J. Assoc. Physicians India* 54:449-452.

RnCeus.com (Aug. 29, 2000). "Serum Creatinine," located at www.rnceus.com/renal/renalcreat.html, three pages, last visited on Mar. 4, 2014, (http://web.archive.org/web/20000829043520/http://www.rnceus.com/renal/renalcreat.html).

Sayed-Ahmed, M.M. et al. (2007). "Thymoquinone Supplementation Prevents the Development of Gentamicin-Induced Acute Renal Toxicity in Rats," *Clinical and Experimental Pharmacology and Physiology* 34:399-405.

Snyder, R.D. et al. (Oct. 1989). "Hyperthermia, Polyamine Depletion, and Inhibition of X-Ray-Induced DNA Strand Break Repair," *Radiation Research* 120(1):121-128.

Snyder, R.D. (1989). "Inhibition of X-ray-induced DNA Strand Break Repair in Polyamine-Depleted HeLa Cells," *International Journal of Radiation Biology* 55(5):773-782.

Solomon, R. et al. (Nov. 24, 1994). "Effects of Saline, Mannitol, and Furosemide on Acute Decreases in Renal Function Induced by Radiocontrast Agents," *The New England Journal of Medicine* 331(21):1416-1420.

Spitz, D.R. et al. (Aug./Dec. 2004). "Metabolic Oxidation/Reduction Reactions and Cellular Responses to Ionizing Radiation: A Unifying Concept in Stress Response Biology," *Cancer and Metastasis Reviews* 23(3/4):311-322.

Wan, X.S. et al. (2006). "Protection Against Radiation-Induced Oxidative Stress in Cultured Human Epithelial Cells by Treatment with Antioxidant Agents," *International Journal of Radiation Oncology Biology Physics* 64(5):1475-1481.

Wu, L-J. et al. (Apr. 1999). "Targeted Cytoplasmic Irradiation with Alpha Particles Induces Mutations in Mammalian Cells," *Proc. Natl. Acad. Sci. USA* 96:4959-4964.

International Preliminary Report on Patentability dated Apr. 19, 2011, for PCT Patent Application No. PCT/US2009/060489, filed on Oct. 13, 2009, seven pages.

International Search Report dated Dec. 10, 2009, for PCT Patent Application No. PCT/US09/60489, filed on Oct. 13, 2009, three pages.

Written Opinion dated Dec. 10, 2009, for PCT Patent Application No. PCT/US09/60489, filed on Oct. 13, 2009, six pages.

Song et al. "Thermodynamic and kinetic considerations for the reaction of semiquinone radicals to form superoxide and hydrogen peroxide", *Free Radic Biol Med.*, Sep. 15, 2010, vol. 49, No. 6, pp. 919-962.

\* cited by examiner

TREATMENT OF OXIDATIVE STRESS DISORDERS INCLUDING CONTRAST NEPHROPATHY, RADIATION DAMAGE AND DISRUPTIONS IN THE FUNCTION OF RED CELLS

CROSS-REFERENCE TO RELATED APPLICATIONS

This application is a filing under 35 U.S.C. § 371 of International Patent Application No. PCT/US2009/060489 having an International Filing Date of Oct. 13, 2009, which claims priority benefit of U.S. Provisional Patent Application No. 61/196,136 filed Oct. 14, 2008. The entire contents of those applications are hereby incorporated by reference herein.

TECHNICAL FIELD

The application discloses compositions and methods useful for treatment or suppression of diseases and symptoms related to oxidative stress affecting normal electron flow in the cells or caused by reactive oxygen species. The state of oxidative stress can be induced by a number of factors, including chemical agents, radiation exposure, and disruptions in the transport of oxygen to tissues.

BACKGROUND

Oxidative stress is caused by disturbances to the normal redox state within cells. An imbalance between routine production and detoxification of reactive oxygen species such as peroxides and free radicals can result in oxidative damage to the cellular structure and machinery.

Oxygen poisoning or toxicity is caused by high concentrations of oxygen that may be damaging to the body and increase the formation of free-radicals and other structures such as nitric oxide, peroxynitrite, and trioxidane. Normally, the body has many defense systems against such damage but at higher concentrations of free oxygen, these systems are eventually overwhelmed with time, and the rate of damage to cell membranes exceeds the capacity of systems which control or repair it. Cell damage and cell death then results.

Qualitative and/or quantitative disruptions in the transport of oxygen to tissues result in energy disruption in the function of red cells and contribute to various diseases such as hemoglobinopathies. Hemoglobinopathy is a genetic defect that results in abnormal structure of one of the globin chains of the hemoglobin molecule. Common hemoglobinopathies include thalassemia and sickle-cell disease. Thalassemia is an inherited autosomal recessive blood disease. In thalassemia, the genetic defect results in reduced rate of synthesis of one of the globin chains that makes up hemoglobin. While thalassemia is a quantitative problem of too few globins synthesized, sickle-cell disease is a qualitative problem of synthesis of an incorrectly functioning globin. Sickle-cell disease is a blood disorder characterized by red blood cells that assume an abnormal, rigid, sickle shape. Sickling decreases the cells' flexibility and results in their restricted movement through blood vessels, depriving downstream tissues of oxygen. In both thalassemia and sickle cell anemia, pathology can result from reactive oxygen species caused by the disruptions in oxygen transport.

Another disorder caused by reactive oxygen species is nephropathy, contrast induced nephropathy (CIN) or contrast nephropathy (CN). Recent research implicates hypoxic tubular injury in the pathophysiology of contrast nephropathy. While intrarenal hypoxia can be caused by systemic transient hypoxemia, increased blood viscosity, and a leftward shift of the oxygen-hemoglobin dissociation curve, imbalance between oxygen demand and supply plays a major role in hypoxic damage to the outer medulla of the kidney caused by contrast media. The outer medulla is normally in a condition of low oxygen tension, due to a limited oxygen supply in the region, a high local metabolic rate, and high oxygen demand, resulting from active salt reabsorption by medullary thick ascending limbs of Henle's loop. Outer medullary physiologic hypoxia is negatively impacted by radiologic contrast agents. Increased metabolic activity and oxygen consumption (due to osmotic diuresis and increased salt delivery to the distal nephron) occurs because the blood flow to this region and the oxygen supply actually increase (Heyman, S N et al, *Invest. Radiol.* (1999), 34 (11) 685-91 and Garofalo A S, *Ren. Fail.* (2007) 29 (2), 121-31).

Contrast agents or dyes, including iodinated contrast solutions, are solutions opaque to x-rays that enable the circulatory system arteries and veins to be visualized, and that enhance the image being obtained. Contrast agents are frequently used in medical procedures. They are frequently administered to patients undergoing radiographic investigations, such as fluoroscopy, x-ray, magnetic resonance, ultrasound imaging and diagnostic angiography. Contrast solutions may also be used in patients undergoing coronary angioplasty or other cardiac catheterization procedures, peripheral vessel studies and placement of pacemaker leads. Delivery of the contrast media into a patient's vasculature enables the vasculature of different organs, tissue types, or body compartments to be more clearly observed or identified.

Radiographic contrast agents can be grouped into two main categories: positive contrast agents and negative contrast agents. Positive contrast media are radiopaque (appearing lighter than surrounding structures) due to their ability to attenuate the X-ray beam. Positive contrast agents contain elements with high atomic weights, (such as iodine, bromine, gadolinium, and barium) which add density to the tissues of interest. Negative contrast agents are radiolucent (darker than surrounding structures) because of their inability to attenuate the X-ray beam. Air and water are examples of negative contrast agents.

Intravascular contrast agents typically comprise iodinated benzene ring derivatives that are formulated as sodium or meglumine salts. The multiple iodine molecules contained within the contrast agent are responsible for the additional attenuation of X-rays in excess of that caused by blood alone. The amount of radiopacity that is generated by a particular contrast agent is a function of the percentage of iodine in the molecule and the concentration of the contrast media administered. The iodine content in different radiographic contrast media can vary from 11% to 48%. With most contrast solutions the iodine content is also proportional to the osmolarity of the contrast agent. Iodinated contrast agents are classified as ionic or high osmolar contrast media (HOCM) or nonionic or low osmolar contrast media (LOCM). The osmolarity of the contrast agent can lead to significant side effects in clinical practice. In general, the lower the osmolarity of the agent the less side effects will occur in the patient.

One of the adverse side effects associated with the use of radiographic contrast media includes nephrotoxicity. In particular, contrast medium-induced nephrotoxicity is known to be an iatrogenic cause of acute renal failure in some patients. It has been reported that use of contrast media is the third most common cause of new onset renal failure in hospital patients. Patients who experience nephrotoxicity may experience changes in serum creatine, or creatine clearance, at about one to five days after receiving the contrast medium. Consequences may be dramatic and can lead to irreversible renal damage and transient or long-term dialysis.

Mild transient decreases in renal function occur after contrast administration in almost all patients. Whether a patient develops clinically significant acute renal failure depends on the presence or absence of certain factors. Factors that may predispose a patient for developing acute renal failure include pre-existing baseline renal insufficiency, diabetes mellitus, cardiovascular disease, including congestive heart failure, aging, and conditions characterized by depletion of effective circulatory volume. Higher doses of contrast media may also increase the risk of contrast nephropathy (CN). Other risk factors include reduced effective arterial volume due for example to dehydration, nephrosis or cirrhosis or concurrent use of potentially nephrotoxic drugs such as nonsteroidal anti-inflammatory agents and ACE (angiotensin-converting enzyme) inhibitors. Patients with preexisting renal impairments and diabetes mellitus have a substantially higher risk of CN than patients with renal impairments alone.

Patients undergoing coronary procedures where contrast enhanced imaging for the interventions are used are at particularly at risk of contrast induced nephropathy. Prevention and mitigation of renal failure after the administration of contrast agent is difficult to achieve. Hydration has been reported to ameliorate contrast nephropathy in chronic renal failure patients (Solomon et al., *N. Engl. J. Med* (1994) 331:1416-20). Ramesh J. et al., *J Assoc Physicians India*. (2006) 54:449-52 suggest that the use of N-Acetyl cysteine could be beneficial for the reduction of renal failure induced by contrast agents.

Accordingly, the problems associated with contrast nephropathy have been a limiting factor to the extent that these advanced angioplasty procedures can be used, particularly in vulnerable populations.

Other causes of nephropathy include, but are not limited to, non-steroidal anti-inflammatory drugs (NSAIDs), amphotericin B, cisplatin, methotrexate, acyclovir, gentamicin, ACE inhibitors, other nephrotoxic drugs, products of tumor lysis syndrome and products of rhabdomyolosis.

An additional cause of oxidative stress is radiation. Radiation is known to produce various reactive oxygen species (ROS) in biological systems such as superoxide, hydrogen peroxide and hydroxyl radical and cause various types of tissue damage due to free radical reactions (Adler V. et al., *Oncogene* 1999 Nov. 1; 18 (45):6104-11). Reactive oxygen species and free radicals react with nucleic acids, lipids, proteins and carbohydrates and induce damage. Cytoplasmic irradiation can result in damage to nuclear DNA. Experiments with free radical scavengers have shown this DNA damage is dependent on ROS generation (Spitz D R, et al. "Metabolic Oxidation/Reduction Reactions and Cellular Responses to Ionizing Radiation: A Unifying Concept in Stress Response Biology." *Cancer and Metastasis Reviews*. (2004) 23:311-322; and Wu L J, et al., "Targeted Cytoplasmic Irradiation with Alpha Particles Induces Mutations in Mammalian Cells." *Proceedings of the National Academy of Sciences*. (1999) 96 (9): 4959-4964).

Exposure to ionizing radiation (such as X-rays, gamma rays and alpha- or beta-radiation) can cause damage to cells. The damage can result in cell death (e.g. through apoptosis), or can cause genetic changes in the cell, resulting in unchecked cell proliferation and cancer. While in general, exposure to such radiation is therefore undesirable, the administration of carefully regulated doses is an accepted treatment for certain cancers. By targeting the radiation to a tumor, cells can be destroyed. A frequent complication of radiotherapy is the irradiation of normal tissues surrounding the cancerous tissues. Such normal tissues are often damaged by the radiation resulting in undesired injury to normal cells and tissues, which can have severe consequences for the affected patient.

Radioprotective agents, also known as radioprotectors, are defined as agents that protect cells or living organisms from deleterious cellular effects of exposure to ionizing radiation. These deleterious cellular effects include damage to cellular DNA, such as DNA strand break, disruption in cellular function, cell death and/or carcinogenesis. The mechanism of the protective effect may at least be partially due to radical scavenging properties and cell cycle modulating properties of the radioprotective agents. These agents, administered prior to, during, and/or after exposure to radiation would eliminate or reduce the severity of deleterious cellular effects caused by exposure to environmental ionizing radiation such as those resulting from a nuclear explosion, a spill of radioactive material, close proximity to radioactive material and the like.

In addition, these agents are believed to provide a selective protection of normal cells and non-cancerous cells during cancer therapy. For example, these agents, administered to the cancer patient prior to or during radiation therapy, will be absorbed by normal, non-cancerous cells to provide a protective effect. However, the radioprotective agents will be absorbed to a lesser or no effect by tumor cells due to their different vascularity and their other known biological differences from normal cells.

The treatment of malignant tumors through the use of radiation is often limited by damage to non-tumor cells. Damage to the non-tumor cells can exceed the effectiveness of the radiation therapy. The main consideration in establishing radiation doses for cancer radiotherapy is the assessment of tolerance of the most radiosensitive normal tissue or organ in the treatment field. Often the maximum tolerable doses are insufficient to eradicate the tumor. Thus the use of a radioprotective agent would greatly increase the tolerable dose, and therefore the prospects of eradication of tumors and treatment of cancer. Cell survival and adaptation to an environment containing radiation can mainly depend on the ability of cells to maintain optimal function in response to free radical-induced damage at the biochemical level. There remains an acute need for non-toxic and effective radioprotectors.

Exposure to radiation can also occur in other ways, including exposure to normal background levels of radiation (such as cosmic rays or radiation due to naturally occurring isotopes present in the earth) or elevated environmental radiation (including occupational exposure of workers in medical facilities working in diagnostic and therapeutic nuclear medicine or of workers in nuclear power plants). Another potential source of exposure to certain types of radiation is accidental or intentional release of radioactive materials, as the result of an accident or of terrorist activity, e.g. as the result of a radiologic weapon such as a so-called "dirty-bomb."

There remains a need in the art for improving patients in need of treatment of diseases related to oxidative stress affecting normal electron flow in the cells induced by chemical agents, radiation and/or disruptions in the transport of oxygen to tissues. The present inventors have unexpectedly discovered that administration of the compounds of this invention are effective in improving the outcome in patients that have been administered contrast media, have suffered from radiation exposure or suffer from hemoglobinopathy.

DISCLOSURE OF THE INVENTION

The present invention is based on the discovery disclosed herein that administration of certain redox-active therapeutics can prevent, reduce or treat diseases related to oxidative stress. The compounds of the present invention may be administered to promote the protection, survival or regeneration of cells, tissues, and/or organs after qualitative and/or quantitative disruptions in the transport of oxygen to tissues that result from energy disruption in red cells. In some embodiments, the energy disruption results from diseases such as hemoglobinopathies. In one embodiment the energy disruption results from thalassemia. In another embodiment the disruption results from sickle cell anemia. In other embodiments, the compounds of the present invention may be administered to treat, prevent, or reduce the severity of renal damage in a patient due to the administration, ingestion, absorption of, or exposure to, a nephrotoxic agent. In other embodiments the compounds of the present invention may be administered to prevent or reduce the effects of radiation in a patient exposed to radiation.

In another embodiment, the invention embraces a method of reducing, preventing or treating a blood disorder characterized by red blood cells that assume an abnormal sickle shape comprising administering to a subject in need thereof a therapeutically effective amount of a redox-active compound of the invention. In another embodiment the invention embraces a method of treating sickle cell anemia comprising administering to a subject in need thereof a therapeutically effective amount of a redox-active compound of the invention. In another embodiment, the invention embraces a method of treating inherited autosomal recessive blood diseases comprising administering to a subject in need thereof a therapeutically effective amount of a redox-active compound of the invention. In another embodiment, the invention embraces a method of treating thalassemia comprising administering to a subject in need thereof a therapeutically effective amount of a redox-active compound of the invention. In one embodiment, the thalassemia is alpha-thalassemia. In another embodiment, the thalassemia is beta-thalassemia. In another embodiment, the thalassemia is beta thalassemia major (that is, Cooley's anemia).

In another embodiment, the invention embraces a method of treating, preventing or reducing the severity of renal damage in a patient due to the administration, ingestion, absorption of, or exposure to a nephrotoxic agent such as a contrast agent comprising administering to a subject in need thereof a therapeutically effective amount of a redox-active compound of the invention. In another embodiment the contrast agent is selected from an iodinated, brominated, barium-containing, and gadolinium-containing contrast agent. In another embodiment, the contrast agent is an iodinated contrast agent selected from diatriozate, metrizoate, ioxaglate, iopamidol, iohexol, ioxilan, iopromide, ioversol, and iodixanol.

In another embodiment, the invention embraces a method of treating, preventing or reducing the severity of renal damage in a patient or subject due to the administration, ingestion, absorption of, or exposure to a nephrotoxic agent comprising a non-steroidal anti-inflammatory drug, cisplatin, methotrexate, acyclovir, gentamicin, ACE inhibitors, or other nephrotoxic drugs, comprising administering to a subject in need thereof a therapeutically effective amount of a redox-active compound of the invention.

In another embodiment, the invention embraces a method of treating, preventing or reducing the effects of radiation injury or radiation damage on normal cells of a patient or subject incurring exposure to radiation, comprising administering to a subject in need thereof a therapeutically effective amount of a redox-active compound of the invention.

In another embodiment, the invention embraces a method of reducing the effect of ionizing radiation on normal cells in a subject at risk of incurring exposure to ionizing radiation comprising administering to said subject prior to, concurrently or after the exposure to radiation, a therapeutically effective amount of a redox-active compound of the invention.

In another embodiment, the invention embraces a method of preventing radiation injury to normal cells in a subject at risk of incurring exposure to ionizing radiation comprising administering to said subject prior, concurrently or after the exposure to radiation, a therapeutically effective amount of a redox-active compound of the invention.

In another embodiment, the invention embraces a method for preventing or reducing radiation injury or radiation damage on normal cells in a mammal exposed to ionization radiation, comprising administering a therapeutically effective amount of a redox-active compound of the invention to the mammal, prior to a radiation exposure.

In another embodiment, the invention embraces a method for preventing or reducing radiation injury or radiation damage on normal cells in a mammal exposed to ionization radiation, comprising administering a therapeutically effective amount of a redox-active compound of the invention to the mammal, subsequent to an accidental or intentional release of radioactive materials.

In another embodiment, the invention embraces a method of preventing death of radiation-damaged or radiation-injured non-cancerous cells with a therapeutically effective amount of a redox-active compound of the invention.

In another embodiment, the invention embraces improved radiotherapy methods for treatment of cancer, comprising administering to a subject a therapeutically effective amount of a redox-active compound of the invention, and then administering to the subject an effective amount of radiation, such that radiation injury to normal cells is decreased or eliminated.

In another embodiment of the invention, including any of the foregoing embodiments, the radiation is selected from the group consisting of diagnosing X-rays, radiotherapy for cancer treatment, CAT-scans, mammograms, radionuclide scans, interventional radiological procedures under computed axial tomography (CAT) or fluoroscopy guidance, tissue-incorporated radionuclides from ingestion of contaminated food or water, and uncontrolled exposure to ionizing radiation from nuclear weapons, radioactive spills and/or cosmic radiation.

In another embodiment of the invention, including any of the foregoing embodiments, the redox-active therapeutics are selected from one or more compounds of Formula I, Formula II, Formula III, Formula IV, Formula V, Formula Va, and Formula VI, and all stereoisomers, mixtures of stereoisomers, prodrugs, metabolites, salts, phosphate substituted forms, crystalline forms, non-crystalline forms, deuterated forms, hydrates or solvates thereof.

In another embodiment of the invention, including any of the foregoing embodiments, the redox-active therapeutics are selected from one or more compounds of Formula I, and all stereoisomers, mixtures of stereoisomers, prodrugs, metabolites, salts, phosphate substituted forms, crystalline forms, non-crystalline forms, deuterated forms, hydrates and solvates thereof.

In another embodiment of the invention, including any of the foregoing embodiments, the redox-active therapeutics are selected from one or more compounds of Formula II, and all stereoisomers, mixtures of stereoisomers, prodrugs, metabolites, salts, phosphate substituted forms, crystalline forms, non-crystalline forms, deuterated forms, hydrates and solvates thereof.

In another embodiment of the invention, including any of the foregoing embodiments, the redox-active therapeutics are selected from one or more compounds of Formula III, and all stereoisomers, mixtures of stereoisomers, prodrugs, metabolites, salts, phosphate substituted forms, crystalline forms, non-crystalline forms, deuterated forms, hydrates and solvates thereof.

In another embodiment of the invention, including any of the foregoing embodiments, the redox-active therapeutics are selected from one or more compounds of Formula IV, and all stereoisomers, mixtures of stereoisomers, prodrugs, metabolites, salts, phosphate substituted forms, crystalline forms, non-crystalline forms, deuterated forms, hydrates and solvates thereof.

In another embodiment of the invention, including any of the foregoing embodiments, the redox-active therapeutics are selected from one or more compounds of Formula V, and Formula Va, and all stereoisomers, mixtures of stereoisomers, prodrugs, metabolites, salts, phosphate substituted forms, crystalline forms, non-crystalline forms, deuterated forms, hydrates and solvates thereof.

In another embodiment of the invention, including any of the foregoing embodiments, the redox-active therapeutics are selected from one or more compounds of Formula VI, and all stereoisomers, mixtures of stereoisomers, prodrugs, metabolites, salts, phosphate substituted forms, crystalline forms, non-crystalline forms, deuterated forms, hydrates and solvates thereof.

In another embodiment of the invention, including any of the foregoing embodiments, the redox-active therapeutics are selected from CoQ10, Idebenone, Ubiquinone, Mitoquinone (Mito-Q) and derivatives thereof.

In another embodiment of the invention, including any of the foregoing embodiments, the redox-active therapeutics are selected from AA-861 (Takeda); E-6700 and E-3300 (Eisai); Seratrodast™ (Abbott); CV-6504 (Takeda); BN-8265 and IRC-083864 (SCRAS); and HU-331 (Hebrew University).

MODES FOR CARRYING OUT THE INVENTION

The invention embraces compounds useful in treating or suppressing diseases and symptoms related to oxidative stress affecting normal electron flow in the cells or caused by reactive oxygen species. The redox-active therapeutics for treatment or suppression of oxidative diseases and associated aspects of the invention are described in more detail herein.

By "subject," "individual," or "patient" is meant an individual organism, preferably a vertebrate, more preferably a mammal, most preferably a human.

Contrast nephropathy can be defined in general as an acute decline in renal function following the administration of intravenous contrast medium. Clinically it is defined as a rise in serum creatine of 0.5 mg/dl, or a rise of 25% or more in the patient's creatine level. The rise in serum creatine usually arises from 24 to 48 hours after the contrast study, generally peaks at 3 to 5 days, and returns to baseline value by 7 to 10 days.

Several mechanisms have been suggested for contrast medium-induced nephropathy. After radiographic contrast medium exposure, a brief period of vasodilation may be followed by renal vasoconstriction leading to intense reduction in renal blood flow, direct toxicity to renal tubular epithelium, tubular obstruction by protein precipitates, complement activation, and renal ischemia. In addition, patients at high risk of developing renal failure, including those with endothelial dysfunction, may not be able to dilate the renal vasculature, and thus experience a prolonged vasoconstrictive response. Vasoconstriction not only causes a decrease in renal blood flow and glomerular filtration rate, but it may also exacerbate medullary ischemia by decreasing oxygen supply since renal oxygen consumption is coupled to renal blood flow.

By "contrast media" is meant any conventional contrast media that may be used at the discretion of the attending physician. Contrast media may include, but are not limited to, iodinated contrast agents, high osmolality contrast agents, low osmolality contrast agents, and biodegradable contrast agents. Contrast media agents may also include contrast agents containing elements with other high atomic weights, such as bromine, gadolinium, and barium Intravascular contrast agents typically comprise iodinated benzene ring derivatives that are formulated as sodium or meglumine salts. The multiple iodine molecules contained within the contrast agent are responsible for the X-ray attenuation. The amount of radiopacity that is generated by a particular contrast agent is a function of the percentage of iodine in the molecule and the concentration of the contrast media administered. The iodine content in different radiographic contrast media can vary from 11% to 48%. Iodinated contrast agents are classified as ionic or high osmolar contrast media (HOCM) or nonionic or low osmolar contrast media (LOCM).

Ionic contrast media dissociate into separate ions, when placed in water solutions, and it is this dissociation that is responsible for increased osmolality in the blood in comparison to nonionic contrast media. Human blood has an osmolality of approximately 300 milliosmoles (mOsm) per kilogram (kg) or 30 mOsm per deciliter (or 30%), while a typical ionic contrast agent can have an osmolality on the order of 1300 mOsm/kg to 1600 mOsm/kg or 130 mOsm per deciliter, making it a hypertonic solution with respect to blood. Some ionic contrast agents include but are not limited to diatriozate, metrizoate and ioxaglate.

The nonionic contrast media do not dissociate into ions, thus resulting in lower osmolality contrast agents. Typical nonionic contrast agents have an osmolality on the order of 500 mOsm/kg to 850 mOsm/kg or 50 mOsm per deciliter to 85 mOsm per deciliter. Although their osmolality is lower than ionic contrast media, they are still considered hypertonic with respect to blood. Some non-ionic contrast agents include but are not limited to iopamidol, ioversol, iohexol, ioxilan, iopromide, and iodixanol.

By "radiation," as used herein, is meant radiation, including ionizing radiation, capable of causing cellular damage. Such forms of radiation include alpha rays, beta rays, x-rays, gamma rays, and neutrons. In one embodiment, ionizing radiation is radiation that has enough energy to eject electrons from electrically neutral atoms, leaving behind charged atoms or ions. In another embodiment, ionizing radiation is a dose of radiation above 155 electron volts that may have carcinogenic, mutagenic, or teratogenic health effects in humans. In another embodiment, alpha rays are alpha radiation or alpha particles (helium nuclei). In another embodiment, beta rays are beta particles (electrons). In another embodiment, high frequency electromagnetic waves, x-rays, are generally identical to gamma rays except for their place of origin. In another embodiment, neutrons are not themselves ionizing but their collisions with nuclei lead to the ejection of other charged particles that do cause ionization. Other forms of radiation sufficiently energetic to cause damage to cells, such as ultraviolet (UV) radiation, are also included. Sources of radiation include radioactive isotopes, which may be naturally-occurring or man-made, and cosmic rays. Radiation can be emitted due to the gradual decay of radioactive isotopes, or due to nuclear fission or fusion events (as in an atomic bomb or nuclear reactor). In certain embodiments, the radiation is x-ray radiation or gamma radiation. In other embodiments, the radiation is beta radiation. In other embodiments, the radiation is alpha radiation. In certain embodiments, the radiation is due to radiation therapy. In certain embodiments, the radiation is radiation due to radioactive fallout or contamination.

The term "radiation damage," as used herein, refers to damage to a nucleic acid molecule in a cell, which damage is caused by exposure of the cell to radiation. For example, radiation exposure can result in double-strand breaks of nucleic acids. As another example, radiation exposure can result in single-strand nicks, breaks, or gaps in nucleic acids, as well as damage to, or loss of, nucleic acid bases. As another example, radiation exposure can result in nucleic acid translocations or various other chromosomal abnormalities. Radiation damage to nucleic acids may be direct or indirect, e.g., radiation may create free radicals, which in turn induce nucleic acid damage. As used herein, the term "preventing radiation damage" means eliminating, ameliorating or decreasing one or more indicia of radiation damage in a treated cell, compared to an untreated cell. As used herein, the term "protecting a cell or subject against radiation damage" means eliminating or decreasing one or more indicia of radiation damage in a treated cell compared to an untreated cell. In one aspect, preventing (or treating) radiation damage in a cell involves decreasing damage to one or more nucleic acid molecules in cells treated according to this invention by at least about 10%, 20%, 30%, 40%, 50%, 80%, 90%, or 95%, compared to untreated cells. In one aspect, preventing (or treating) radiation damage means enhancing DNA repair in a normal cell.

By non-steroidal anti-inflammatory drugs, (NSAIDs), are meant drugs with analgesic, antipyretic and, in higher doses, anti-inflammatory effects, reducing pain, fever and inflammation. The term "non-steroidal" is used to distinguish these drugs from steroids, which have a similar eicosanoid-depressing, anti-inflammatory action. As analgesics, NSAIDs are unusual in that they are non-narcotic. The most prominent members of this group of drugs are aspirin, ibuprofen, and naproxen partly because they are available over-the-counter in many areas.

By "ACE inhibitors," or inhibitors of Angiotensin-Converting Enzyme, is meant a group of pharmaceuticals that are used primarily in treatment of hypertension and congestive heart failure. Some examples of ACE inhibitors are captopril, zofenopril, enalapril, ramipril, quinapril, perindopril, lisinopril, benazepril and fosinopril. Adverse drug reactions (=1% of patients) include renal impairment.

"Treating" a disease with the compounds and methods discussed herein is defined as administering one or more of the compounds discussed herein, with or without additional therapeutic agents, in order to reduce or eliminate either the disease or one or more symptoms of the disease, or to retard the progression of the disease or of one or more symptoms of the disease, or to reduce the severity of the disease or of one or more symptoms of the disease. "Suppression" of a disease with the compounds and methods discussed herein is defined as administering one or more of the compounds discussed herein, with or without additional therapeutic agents, in order to suppress the clinical manifestation of the disease, or to suppress the manifestation of adverse symptoms of the disease. The distinction between treatment and suppression is that treatment occurs after adverse symptoms of the disease are manifest in a subject, while suppression occurs before adverse symptoms of the disease are manifest in a subject. Suppression may be partial, substantially total, or total. The compounds and methods of the invention can then be administered to asymptomatic patients at risk of developing the clinical symptoms of the disease, in order to suppress the appearance of any adverse symptoms, for example the compounds of the invention can be administered to patients undergoing radiotherapy at risk of radiation damage or injury. "Therapeutic use" of the compounds discussed herein is defined as using one or more of the compounds discussed herein to treat or suppress a disease, as defined above. A "therapeutically effective amount" of a compound is an amount of the compound, which, when administered to a subject, is sufficient to reduce or eliminate either a disease or one or more symptoms of a disease, or to retard the progression of a disease or of one or more symptoms of a disease, or to reduce the severity of a disease or of one or more symptoms of a disease, or to suppress the clinical manifestation of a disease, or to suppress the manifestation of adverse symptoms of a disease. A therapeutically effective amount can be given in one or more administrations.

As used herein, "redox-active therapeutics" embraces therapeutics comprising a moiety having the property of giving up electrons to a suitable oxidizing agent or taking up electrons from a suitable reducing agent. For the purposes of the present invention, the preferred moieties comprise a quinone core structure. Examples of redox-active therapeutics are CoQ10, Idebenone, Ubiquinone, Mitoquinone (Mito-Q) and their derivatives. Further examples of redox-active therapeutics are provided in co-assigned US Pat. Publications Nos. 2009/0118257, 2006/0281809, 2007/0072943, 2007/0225261, and International Pat. Publication No. WO 2009/089224, incorporated herein by reference. Other examples of therapeutics having chemical structures comprising a quinone moiety included in but not limiting the invention are AA-861 (Takeda); E-6700 and E-3300 (Eisai); Seratrodast™ (Abbott); CV-6504 (Takeda); BN-8265 and IRC-083864 (SCRAS); and HU-331 (Hebrew University). For the purpose of the present invention the quinone moiety in the chemical structure of the redox-active therapeutic may be isolated or embedded in a larger structure such as but not limited to a naphthoquinone, anthraquinone or a larger molecule such as Mitomycin. For the purpose of the present invention the quinone moiety in the chemical structure of the redox-active therapeutic may occur as its oxidized (cyclohexadienedione) quinone form or its reduced (benzenediol) hydroquinone form. For the purpose of the present invention the term includes pro-drugs of the redox-active compounds as defined herein. For the purpose of the invention, the term includes derivatives of the redox-active compounds defined herein, wherein one or more hydrogen atoms have been replaced by a hydrogen isotope, for example by deuterium. For the purpose of the present invention, the term excludes β-Lapachone.

Examples of Redox-Active Therapeutic Compounds.

Some redox-active therapeutic compounds used in the methods of treatment of the present invention are selected from compounds of Formula I:

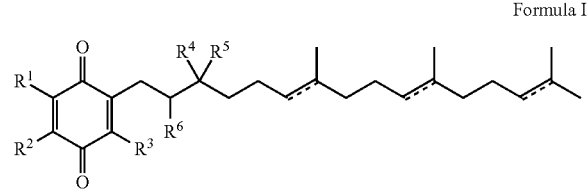

Formula I wherein,
the bonds indicated with a dashed line can be all single or all double,
$R^1$, $R^2$, and $R^3$ are independently selected from H, $(C_1-C_4)$-alkyl, $(C_1-C_4)$-haloalkyl, —CN, —F, —Cl, —Br, and —I; and
$R^4$ and $R^5$ are independently selected from hydroxy and $(C_1-C_4)$-alkyl, and $R^6$ is hydrogen; or
$R^4$ is $(C_1-C_4)$-alkyl, and $R^5$ and $R^6$ are hydrogen; or
$R^4$ is $(C_1-C_4)$-alkyl, and $R^5$ and $R^6$ together form the second bond of a double bond between the carbon atoms to which they are attached;
and all stereoisomers, mixtures of stereoisomers, prodrugs, metabolites, salts, phosphate substituted forms, crystalline forms, non-crystalline forms, deuterated forms, hydrates and solvates thereof.

Some other redox-active therapeutic compounds used in the methods of treatment of the present invention are selected from compounds of Formula II:

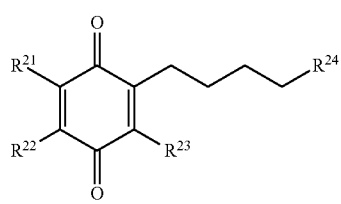

Formula II wherein,
$R^{21}$, $R^{22}$, and $R^{23}$ are independently selected from H, $(C_1-C_4)$-alkyl, $(C_1-C_4)$-haloalkyl, —CN, —F, —Cl, —Br, and —I;
$R^{24}$ is independently selected from $(C_1-C_{20})$-alkyl, $(C_2-C_{20})$-alkenyl, $(C_2-C_{20})$-alkynyl, and a $(C_1-C_{20})$ group containing at least one double bond and at least one triple bond;
and all stereoisomers, mixtures of stereoisomers, prodrugs, metabolites, salts, phosphate substituted forms, crystalline forms, non-crystalline forms, deuterated forms, hydrates and solvates thereof.

Some other redox-active therapeutic compounds used in the methods of treatment of the present invention are selected from compounds of Formula III:

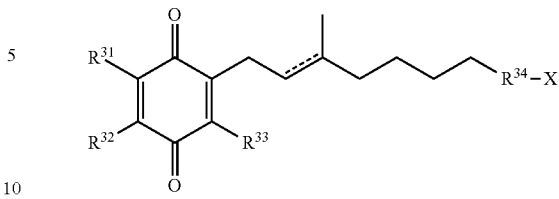

Formula III wherein,
the bond indicated with a dashed line can be single or double;
$R^{31}$, $R^{32}$, and $R^{33}$ are independently selected from the group consisting of H, $(C_1-C_5)$-alkyl, $(C_1-C_5)$-haloalkyl, $(C_2-C_5)$-alkenyl, $(C_2-C_5)$-haloalkenyl, $(C_2-C_5)$-alkynyl, —$(C_2-C_5)$-haloalkynyl, —$OR^{35}$, —$SR^{35}$, —CN, —F, —Cl, —Br, —I, —$N_3$, and $NR^{35}R^{36}$; where $R^{35}$ and $R^{36}$ are independently selected from the group consisting of H, $(C_1-C_5)$-alkyl, $(C_3-C_5)$-cycloalkyl, $(C_1-C_5)$-haloalkyl, aryl, heteroaryl, —(C=O)—$(C_0-C_8)$-alkyl, and —(C=O)—$(C_0-C_8)$-alkyl-$(C_6-C_{10})$-aryl-$(C_0-C_8)$-alkyl, or where $R^{35}$ and $R^{36}$ selected from these groups are combined to form a ring;
$R^{34}$ represents a linear or branched group containing 1 to 32 carbon atoms and any number of single, double, or triple bonds in any chemically possible combination;
X is selected from the group consisting of H, —F, —Cl, —Br, —I, —CN, —$N_3$, —$NR^{37}R^{38}$, and —$OR^{39}$; where $R^{37}$ and $R^{38}$ are independently selected from H, $(C_1-C_8)$-alkyl or $(C_1-C_8)$-haloalkyl, —(C=O)—$(C_1-C_8)$-alkyl, or
  where one of $R^{37}$ and $R^{38}$ are independently selected from
    the group consisting of —(C=O)—$(C_0-C_8)$-haloalkyl; —(C=O)—$NH_2$; —(C=O)—NH$(C_1-C_8)$-alkyl; —(C=O)—NH$(C_1-C_8)$-haloalkyl; —(C=O)—$NR^{301}R^{302}$, where $R^{301}$ and $R^{302}$ together with the nitrogen atom to which they are attached combine to form a 3- to 8-membered ring, and where another group selected from —NH—, —N($(C_1-C_4)$-alkyl)-, —O—, or —S— can be optionally incorporated in the ring formed by $R^{301}$ and $R^{302}$ and the nitrogen atom to which they are attached; —(C=O)—O—$(C_1-C_8)$-alkyl, —(C=O)—O—$(C_1-C_8)$-haloalkyl, —$S(O)_2$—$(C_1-C_8)$-alkyl, —$S(O)_2$-aryl, and —$S(O)_2$-aralkyl,
  and where the other of $R^{37}$ or $R^{38}$ is H, $(C_1-C_8)$-alkyl or $(C_1-C_8)$-haloalkyl or where $R^{37}$ and $R^{38}$ selected from these groups together with the nitrogen atom to which they are attached combine to form a 3- to 8-membered ring, and where another group selected from —NH—, —N($(C_1-C_4)$-alkyl)-, —O—, or —S— can be optionally incorporated in the ring formed by $R^{37}$ and $R^{38}$ and the nitrogen atom to which they are attached;
where $R^{39}$ is independently selected from H, —$(C_1-C_8)$-alkyl or $(C_1-C_8)$-haloalkyl, —(C=O)—$(C_1-C_8)$-alkyl, —(C=O)—$(C_1-C_8)$-haloalkyl, —(C=O)—$NH_2$, —(C=O)—NH—$(C_1-C_8)$-alkyl, —(C=O)—NH$(C_1-C_8)$-haloalkyl, —(C=O)—$NR^{301}R^{302}$ where $R^{301}$ and $R^{302}$ together with the nitrogen atom to which they are attached combine to form a 3- to 8-membered ring, and where another group selected from —NH—, —N($(C_1-C_4)$-alkyl)-, —O—, or —S— can be optionally incorporated in the ring formed by $R^{301}$ and $R^{302}$ and the nitrogen atom to which they are attached, —(C=O)—O—$(C_1-C_8)$-alkyl, —(C=O)—O—$(C_1-C_8)$-haloalkyl, —$S(O)_2$—$(C_1-C_8)$-alkyl, —$S(O)_2$-aryl, and —$S(O)_2$-aralkyl;

with the proviso that when both of $R^{31}$ and $R^{32}$ are —OCH$_3$ and $R^{33}$ is —CH$_3$, then X is not —H or —OH;

and all stereoisomers, mixtures of stereoisomers, prodrugs, metabolites, salts, phosphate substituted forms, crystalline forms, non-crystalline forms, deuterated forms, hydrates and solvates thereof.

Some other redox-active therapeutic compounds used in the methods of treatment of the present invention are selected from compounds of Formula IV:

Formula IV wherein, n is an integer from 0 to 9 inclusive;

the bond indicated with dashed lines can be single or double, and in each unit the dashed bond can single or double independently of other units;

$R^{41}$, $R^{42}$, and $R^{43}$ are independently selected from the group consisting of H, (C$_1$-C$_5$)-alkyl, (C$_1$-C$_5$)-haloalkyl, (C$_2$-C$_5$)-alkenyl, (C$_2$-C$_5$)-haloalkenyl, (C$_2$-C$_5$)-alkynyl, (C$_2$-C$_5$)-haloalkynyl, —OR$^{45}$, —SR$^{45}$, —CN, —F, —Cl, —Br, —I, —N$_3$, and —NR$^{45}$R$^{46}$; where R$^{45}$ and R$^{46}$ are independently selected from the group consisting of H, (C$_1$-C$_5$)-alkyl, (C$_3$-C$_6$)-cycloalkyl, (C$_1$-C$_5$)-haloalkyl, aryl, heteroaryl, —(C=O)—(C$_0$-C$_8$)-alkyl, and —(C=O)—(C$_0$-C$_8$)-alkyl-(C$_6$-C$_{10}$)aryl-(C$_0$-C$_4$)alkyl, or where R$^{45}$ and R$^{46}$ selected from these groups are combined to form a ring;

$R^{44}$ is selected from the group consisting of H, —OR$^{45}$, —SR$^{45}$, —F, —Cl, —Br, —I, and —NR$^{45}$R$^{46}$;

X is selected from the group consisting of H, —NR$^{47}$R$^{48}$, —OR$^{49}$ and —(CH$_2$)$_2$C(CH$_3$)$_2$OH;

$R^{47}$ and $R^{48}$ are independently selected from H, —(C$_1$-C$_8$)-alkyl or (C$_1$-C$_8$)haloalkyl, —(C=O)—(C$_0$-C$_8$)-alkyl, or where either one of R$^{47}$ and R$^{48}$ are independently selected from the group consisting of —(C=O)—(C$_0$-C$_8$)-haloalkyl, —(C=O)—NH$_2$, —(C=O)—(C$_1$-C$_8$)alkyl, —(C=O)—NH(C$_0$-C$_8$)-haloalkyl, —(C=O)—NR$^{401}$R$^{402}$ where R$^{401}$ and R$^{402}$ together with the nitrogen atom to which they are attached combine to form a 3- to 8-membered ring, and where another group selected from —NH—, —N((C$_1$-C$_4$)alkyl)-, —O—, or —S— can be optionally incorporated in the ring formed by R$^{401}$ and R$^{402}$ and the nitrogen atom to which they are attached; —(C=O)—O—(C$_1$-C$_8$)alkyl, —(C=O)—O(C$_1$-C$_8$)-haloalkyl, —S(O)$_2$—(C$_0$-C$_8$)-alkyl, —S(O)$_2$-aryl, and —S(O)$_2$-aralkyl, and where the other of R$^{47}$ or R$^{48}$ is H, (C$_1$-C$_8$)-alkyl or (C$_1$-C$_8$)-haloalkyl or where R$^{47}$ and R$^{48}$ selected from these groups are combined to form a ring, or where R$^{47}$ and R$^{48}$ together with the nitrogen atom to which they are attached combine to form a 3- to 8-membered ring, and where another group selected from —NH—, —N((C$_1$-C$_4$)-alkyl)-, —O—, or —S— can be optionally incorporated in the ring formed by R$^{47}$ and R$^{48}$ and the nitrogen atom to which they are attached; where R$^{49}$ is independently selected from H, (C$_1$-C$_8$)-alkyl or (C$_1$-C$_8$)-haloalkyl, —(C=O)—(C$_1$-C$_8$)-alkyl, —(C=O)—(C$_1$-C$_8$)haloalkyl, —(C=O)—NH$_2$, —(C=O)—(C$_1$-C$_8$)-alkyl, —(C=O)—NH(C$_1$-C$_8$)-haloalkyl, —(C=O)—NR$^{401}$R$^{402}$ where R$^{401}$ and R$^{402}$ together with the nitrogen atom to which they are attached combine to form a 3- to 8-membered ring, and where another group selected from —NH—, —N((C$_1$-C$_4$)-alkyl)-, —O—, or —S— can be optionally incorporated in the ring formed by R$^{401}$ and R$^{402}$ and the nitrogen atom to which they are attached; —(C=O)—NH(C$_1$-C$_8$)-alkyl, —(C=O)—O(C$_1$-C$_8$)-haloalkyl, —S(O)$_2$—(C$_1$-C$_8$)-alkyl, —S(O)$_2$-aryl, and —S(O)$_2$-aralkyl; with the provisos that when n=3 and if R$^{44}$ is —H or —OH, then X is not —H, and that when R$^{41}$ and R$^{42}$ are —OCH$_3$ and R$^{43}$ is —CH$_3$, then either R$^{44}$ is neither H nor —OH, or X is neither H nor —OH nor —(CH2)$_2$C(CH$_3$)$_2$OH;

and stereoisomers, mixtures of stereoisomers, prodrugs, metabolites, salts, phosphate substituted forms, crystalline forms, non-crystalline forms, deuterated forms, hydrates and solvates thereof.

Some other redox-active therapeutic compounds used in the methods of treatment of the present invention are selected from compounds of Formula V and Formula Va:

Formula V wherein, $R^{51}$, $R^{52}$, and $R^{53}$ are independently selected from hydrogen and (C$_1$-C$_6$)-alkyl;

$R^{54}$ is (C$_1$-C$_6$)-alkyl;

$R^{55}$ and $R^{56}$ are independently selected from hydrogen, hydroxy, alkoxy, (C$_1$-C$_{40}$)-alkyl, (C$_2$-C$_{40}$)-alkenyl, (C$_2$-C$_{40}$)-alkynyl, and aryl; where the alkyl, alkenyl, alkynyl or aryl groups may optionally be substituted with —OR$^{501}$, —S(O)$_{0-2}$R$^{501}$, —CN, —F, —Cl, —Br, —I, —NR$^{501}$R$^{502}$, oxo (on an atom with two available valences), (C$_3$-C$_6$)-cycloalkyl, aryl, aryl-(C$_1$-C$_6$)-alkyl, heteroaryl, heterocyclyl, —C(=O)—R$^{503}$, —C(=O)—(C$_0$-C$_6$)-alkyl-aryl, —C(=O)—O—R$^{503}$, —C(=O)—O—(C$_0$-C$_6$)-alkyl-aryl, —C(=O)—N—R$^{503}$R$^{504}$, —C(=O)—N—(C$_0$-C$_6$)-alkyl-aryl, —N—C(=O)—R$^{503}$, —N—C(=O)—(C$_0$-C$_6$)-alkyl-aryl; where the aryl, heteroaryl and heterocyclyl ring substituents may be further substituted with (C$_1$-C$_6$)-alkyl, (C$_1$-C$_6$)-haloalkyl, oxo (on an atom with two available valences), hydroxy, (C$_1$-C$_6$)-alkoxy, —C(=O)—(C$_1$-C$_6$)-alkyl and —C(=O)—O—(C$_1$-C$_6$)-alkyl; and where one of the carbons of the alkyl, alkenyl, or alkynyl groups may be substituted with a heteroatom selected from O, N or S; or $R^{55}$ and $R^{56}$ together with the atom to which they are attached form a saturated or unsaturated 3-8 membered ring, optionally incorporating one or more additional, such as one, two, or three, N, O, or S atoms, optionally substituted with oxo (on an atom with two available valences), —OR$^{501}$, —SR$^{501}$, —CN, —F, —Cl, —Br, —I, —NR$^{501}$R$^{502}$, (C$_1$-C$_6$)-alkyl, (C$_1$-C$_6$)-haloalkyl; hydroxy-(C$_1$-C$_6$)-alkyl, —C(=O)—H, —C(=O)—(C$_1$-C$_6$)-alkyl, —C(=O)-aryl, —C(=O)—OH, or —C(=O)—O—(C$_1$-C$_6$)-alkyl; or $R^{55}$ and $R^{56}$ together with the nitrogen atom to which they are attached form an N,N'-disubstituted piperazine where the nitrogen substitution at the 4-position is a group identical to the substitution at the 1-position forming a compound of formula Va, where $R^{51}$, $R^{52}$, $R^{53}$, and $R^{54}$ are as defined above:

Formula Va

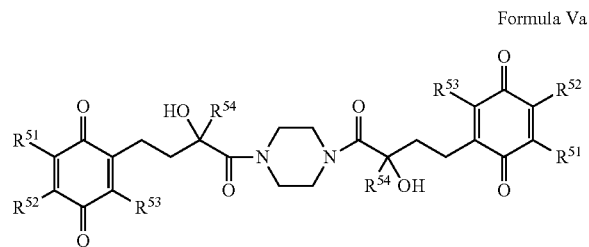

$R^{501}$ and $R^{502}$ are independently selected from the group consisting of hydrogen, $(C_1-C_6)$-alkyl, $(C_1-C_6)$-haloalkyl, aryl, aryl-$(C_1-C_6)$-alkyl, heteroaryl, heterocyclyl, —C(═O)—H, —C(═O)—$(C_1-C_6)$-alkyl, —C(═O)-aryl and —C(═O)—$(C_1-C_6)$-alkyl-aryl; and $R^{503}$ and $R^{504}$ are selected from hydrogen and $(C_1-C_6)$-alkyl; and all stereoisomers, mixtures of stereoisomers, prodrugs, metabolites, salts, phosphate substituted forms, crystalline forms, non-crystalline forms, deuterated forms, hydrates and solvates thereof.

Some other redox-active therapeutic compounds used in the methods of treatment of the present invention are selected from compounds of Formula VI:

Formula VI

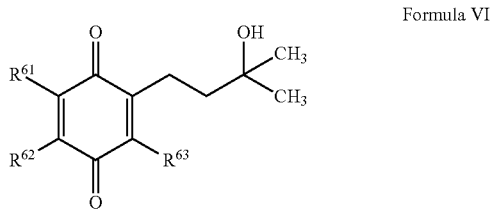

wherein, $R^{61}$ is aryl-$(C_0-C_6)$-alkyl- or heterocyclyl-$(C_0-C_6)$-alkyl-, wherein the aryl or heterocyclyl is optionally substituted with one or more substituents selected from $(C_1-C_6)$-alkyl, $(C_2-C_6)$-alkenyl, $(C_2-C_6)$-alkynyl, halogen, $(C_1-C_6)$-haloalkyl, hydroxy, $(C_1-C_6)$-alkoxy, —CN, nitro, —C(═O)$OR^{64}$, —$NR^{65}R^{66}$, —C(═O)$NR^{65}R^{66}$, —SH, —S—$(C_1-C_6)$ alkyl, and —C(═O)$R^{64}$; and wherein the $(C_0-C_6)$-alkyl group is optionally substituted with OH, —O—$(C_1-C_4)$-alkyl, —$NH_2$, —$NH(C_1-C_4)$-alkyl, —N$((C_1-C_4)$-alkyl$)_2$, oxo (on an atom with two available valences) or halogen; and $R^{62}$ and $R^{63}$ are independently selected from hydrogen, halogen, $(C_1-C_6)$-alkyl and $(C_1-C_6)$-alkoxy; or $R^{63}$ is aryl-$(C_0-C_6)$-alkyl- or heterocyclyl-$(C_0-C_6)$-alkyl-, wherein the aryl or heterocyclyl is optionally substituted with one or more substituents selected from $(C_1-C_6)$-alkyl, $(C_2-C_6)$-alkenyl, $(C_2-C_6)$-alkynyl, halogen, $(C_1-C_6)$-haloalkyl-, hydroxy, $(C_1-C_6)$-alkoxy, CN, nitro, —C(═O)$OR^{64}$, —$NR^{65}R^{66}$, —C(═O)$NR^{65}R^{66}$, —SH, —S—$(C_1-C_6)$ alkyl, and —C(═O)$R^{64}$; and wherein the $(C_0-C_6)$-alkyl group is optionally substituted with OH, —O$(C_1-C_4)$-alkyl, —$NH_2$, —$NH(C_1-C_4)$-alkyl, —N$((C_1-C_4)$-alkyl$)_2$, oxo (on an atom with two available valences) or halogen; and $R^{61}$ and $R^{62}$ are independently selected from hydrogen, halogen, $(C_1-C_6)$-alkyl, and $(C_1-C_6)$-alkoxy;

$R^{64}$ is hydrogen, $(C_1-C_6)$-alkyl, aryl, or aryl-$(C_1-C_6)$-alkyl-;

$R^{65}$ and $R^{66}$ are independently of each other hydroxy, $(C_1-C_6)$-alkoxy, $(C_1-C_6)$-alkyl, $(C_2-C_6)$-alkenyl, $(C_2-C_6)$-alkynyl, aryl, aryl-$(C_1-C_6)$-alkyl-, heterocyclyl, or heterocyclyl-$(C_1-C_6)$-alkyl-; wherein the alkyl, alkenyl, alkynyl, aryl and heterocyclyl groups can be further substituted with oxo (on an atom with two available valences), halogen, $(C_1-C_6)$-haloalkyl, hydroxy, $(C_1-C_6)$-alkoxy, or —C(═O)$OR^{64}$;

and all stereoisomers, mixtures of stereoisomers, prodrugs, metabolites, salts, phosphate substituted forms, crystalline forms, non-crystalline forms, deuterated forms, hydrates and solvates thereof.

Some examples of redox-active therapeutics described in co-assigned US publications 2006/0281809, 2007/0072943, and 2007/0225261 are:

alpha-tocopherol quinone (alternatively named as 2-(3-hydroxy-3,7,11,15-tetramethylhexadecyl)-3,5,6-trimethyl-cyclohexa-2,5-diene-1,4-dione);

2,3,5-trimethyl-6-(3,7,11,15-tetramethyl-hexadecyl)-[1,4]benzoquinone;

beta-tocopherol quinone;

gamma-tocopherol quinone;

alpha-tocotrienol quinone (alternatively named as 2-(3-hydroxy-3,7,11,15-tetramethyl-6,10,14-hexadecatrienyl)-3,5,6-trimethyl-2,5-cyclohexadiene-1,4-dione or 2-(3-hydroxy-3,7,11,15-tetramethyl-6,10,14-hexadecatrienyl)-3,5,6-trimethyl-p-benzoquinone, CAS Registry number 14101-66-7);

beta-tocotrienol quinone;

gamma-tocotrienol quinone;

2,3,5-trimethyl-6-(3,7,11,15-tetramethylhexadecyl)-2,5-cyclohexadiene-1,4-dione;

2,3,5-trimethyl-6-(3,7,11,15-tetramethyl-2,6,10,14-hexadecatetraenyl)-2,5-cyclohexadiene-1,4-dione;

2-butyl-3-(3-hydroxy-3,7,11,15-tetramethylhexadecyl)-5,6-dimethylcyclohexa-2,5-diene-1,4-dione;

2,3,5-trimethyl-6-(3,7,11,15-tetramethyl-hexadeca-2,6,10,14-tetraenyl)-[1,4]benzoquinone;

2-butyl-3-(3-hydroxy-3,7,11,15-tetramethyl-hexadecyl)-5,6-dimethyl-[1,4]benzoquinone;

2-(3-hydroxy-3,7,11,15-tetramethyl-hexadecyl)-5,6-dimethyl-3-propyl-[1,4]benzoquinone;

3-(3-hydroxy-3,7,11,15-tetramethyl-hexadecyl)-5-methyl-2-propyl-[1,4]benzoquinone;

2-(3-hydroxy-3,7,11,15-tetramethyl-hexadecyl)-3-isobutyl-5,6-dimethyl-[1,4]benzoquinone;

3-hydroxy-3,7,11,15-tetramethylhexadecyl]-3,5,6-trimethyl-2,5-cyclohexadiene-1,4-dione;

2-hexyl-3,5,6-trimethyl-[1,4]benzoquinone;

2-octyl-3,5,6-trimethyl-[1,4]benzoquinone;

2-heptadeca-8,11-dienyl-3,5,6-trimethyl-[1,4]benzoquinone;

2-heptadec-8-enyl-3,5,6-trimethyl-[1,4]benzoquinone;

2-tert-butyl-3-hexyl-5,6-dimethyl-[1,4]benzoquinone;

2-heptadeca-8,11-dienyl-3,5-diisopropyl-6-methyl-[1,4]benzoquinone;

2-heptyl-3,5-diisopropyl-6-methyl-[1,4]benzoquinone;

2,3-dimethyl-5,6-bis-(3-methyl-butyl)-[1,4]benzoquinone;

2-(3-hydroxy-3-methyl-butyl)-5,6-dimethyl-3-(3-methyl-but-2-enyl)-[1,4]benzoquinone;

2-(3-hydroxy-3-methyl-butyl)-5,6-dimethyl-3-(3-methyl-butyl)-[1,4]benzoquinone;

2-(7-chloro-3-methylhept-2-enyl)-3,5,6-trimethylcyclohexa-2,5-diene-1,4-dione;

2-(6-chloro-3-methylhex-2-enyl)-3,5,6-trimethylcyclohexa-2,5-diene-1,4-dione;
2-(6-iodo-3-methylhex-2-enyl)-3,5,6-trimethylcyclohexa-2,5-diene-1,4-dione;
2,3,5-trimethyl-6-(3-methylnon-2-enyl)-1,4-benzoquinone;
5-methyl-7-(2,4,5-trimethyl-3,6-dioxocyclohexa-1,4-dienyl)hept-5-enenitrile;
N-(5-methyl-7-(2,4,5-trimethyl-3,6-dioxocyclohexa-1,4-dienyl)hept-5-enyl)acetamide;
5-methyl-7-(2,4,5-trimethyl-3,6-dioxocyclohexa-1,4-dienyl)hept-5-enal;
2-(7-hydroxy-3-methylhept-2-enyl)-3,5,6-trimethylcyclohexa-2,5-diene-1,4-dione
2-tert-butyl-5,6-dimethyl-3-(3-methylnon-2-enyl)cyclohexa-2,5-diene-1,4-dione
2-(3,16-dihydroxy-3,7,11,15-tetramethylhexadeca-6,10,14-trienyl)-3,5,6-trimethylcyclohexa-2,5-diene-1,4-dione;
2-(16-amino-3-hydroxy-3,7,11,15-tetramethylhexadeca-6,10,14-trienyl)-3,5,6-trimethylcyclohexa-2,5-diene-1,4-dione;
2-(15-hydroxy-3,7,11,15-tetramethylhexadecyl)-3,5,6-trimethylcyclohexa-2,5-diene-1,4-dione;
2-(3-chloro-15-hydroxy-3,7,11,15-tetramethylhexadecyl)-3,5,6-trimethylcyclohexa-2,5-diene-1,4-dione
2-(3-chloro-15-hydroxy-3,7,11,15-tetramethylhexadeca-6,10-dienyl)-3,5,6-trimethylcyclohexa-2,5-diene-1,4-dione
2-(3-hydroxy-3-methylbutyl)-3-isopentyl-5,6-dimethylcyclohexa-2,5-diene-1,4-dione;
2,3-diisopentyl-5,6-dimethylcyclohexa-2,5-diene-1,4-dione
7-5-methyl-7-(2,4,7-trimethyl-3,6-dioxocyclohexa-1,4-dienyl)hept-5-enyl acetate; and
2-(7-hydroxy-3-methylhept-2-enyl)-3,5,6-trimethylcyclohexa-2,5-diene-1,4-dione;
and all stereoisomers, mixtures of stereoisomers, prodrugs, metabolites, salts, phosphate substituted forms, crystalline forms, non-crystalline forms, deuterated forms, hydrates and solvates thereof.

Some examples of redox-active therapeutics described in co-assigned U.S. provisional applications US Pat. Publications Nos. 2009/0118257 and International Pat. Publication No. WO/2009/089224 are:
6,6'-(4,4'-(piperazine-1,4-diyl)bis(3-hydroxy-3-methyl-4-oxobutane-4,1-diyl))bis(2,3,5-trimethylcyclohexa-2,5-diene-1,4-dione);
2-hydroxy-N-(2-hydroxyethyl)-2-methyl-4-(2,4,5-trimethyl-3,6-dioxocyclohexa-1,4-dienyl)butanamide;
2-(3-hydroxy-3-methyl-4-oxo-4-(piperidin-1-yl)butyl)-3,5,6-trimethylcyclohexa-2,5-diene-1,4-dione;
N-hexyl-2-hydroxy-2-methyl-4-(2,4,5-trimethyl-3,6-dioxocyclohexa-1,4-dienyl)butanamide;
N-benzyl-2-hydroxy-2-methyl-4-(2,4,5-trimethyl-3,6-dioxocyclohexa-1,4-dienyl)butanamide;
N-(cyclopropylmethyl)-2-hydroxy-2-methyl-4-(2,4,5-trimethyl-3,6-dioxocyclohexa-1,4-dienyl)butanamide;
2-hydroxy-2-methyl-N-phenethyl-4-(2,4,5-trimethyl-3,6-dioxocyclohexa-1,4-dienyl)butanamide;
2-hydroxy-N-(3-hydroxypropyl)-2-methyl-4-(2,4,5-trimethyl-3,6-dioxocyclohexa-1,4-dienyl)butanamide;
N-cyclopropyl-2-hydroxy-2-methyl-4-(2,4,5-trimethyl-3,6-dioxocyclohexa-1,4-dienyl)butanamide;
2-(3-hydroxy-4-(4-hydroxypiperidin-1-yl)-3-methyl-4-oxobutyl)-3,5,6-trimethylcyclohexa-2,5-diene-1,4-dione;
2-hydroxy-2-methyl-4-(2,4,5-trimethyl-3,6-dioxocyclohexa-1,4-dienyl)butanamide;
2-hydroxy-N-(4-hydroxybutyl)-2-methyl-4-(2,4,5-trimethyl-3,6-dioxocyclohexa-1,4-dienyl)butanamide;
2-hydroxy-N-(5-hydroxypentyl)-2-methyl-4-(2,4,5-trimethyl-3,6-dioxocyclohexa-1,4-dienyl)butanamide;
2-hydroxy-N-(1-hydroxypropan-2-yl)-2-methyl-4-(2,4,5-trimethyl-3,6-dioxocyclohexa-1,4-dienyl)butanamide;
methyl 2-(2-hydroxy-2-methyl-4-(2,4,5-trimethyl-3,6-dioxocyclohexa-1,4-dienyl)butanamido)acetate;
N-(3-(1H-imidazol-1-yl)propyl)-2-hydroxy-2-methyl-4-(2,4,5-trimethyl-3,6-dioxocyclohexa-1,4-dienyl)butanamide;
2-hydroxy-N-(2-(2-hydroxyethoxy)ethyl)-2-methyl-4-(2,4,5-trimethyl-3,6-dioxocyclohexa-1,4-dienyl)butanamide;
2-hydroxy-2-methyl-N-(pyridin-2-ylmethyl)-4-(2,4,5-trimethyl-3,6-dioxocyclohexa-1,4-dienyl)butanamide;
2-hydroxy-2-methyl-N-(3-(2-oxopyrrolidin-1-yl)propyl)-4-(2,4,5-trimethyl-3,6-dioxocyclohexa-1,4-dienyl)butanamide;
2-hydroxy-N-(6-hydroxyhexyl)-2-methyl-4-(2,4,5-trimethyl-3,6-dioxocyclohexa-1,4-dienyl)butanamide;
2-(3-hydroxy-3-methyl-4-(4-methylpiperazin-1-yl)-4-oxobutyl)-3,5,6-trimethylcyclohexa-2,5-diene-1,4-dione;
2-(4-(4-benzylpiperazin-1-yl)-3-hydroxy-3-methyl-4-oxobutyl)-3,5,6-trimethylcyclohexa-2,5-diene-1,4-dione;
2-hydroxy-2-methyl-N-(3-morpholinopropyl)-4-(2,4,5-trimethyl-3,6-dioxocyclohexa-1,4-dienyl)butanamide;
2-hydroxy-N,N-bis(2-hydroxyethyl)-2-methyl-4-(2,4,5-trimethyl-3,6-dioxocyclohexa-1,4-dienyl)butanamide;
N-(2-(dimethylamino)ethyl)-2-hydroxy-2-methyl-4-(2,4,5-trimethyl-3,6-dioxocyclohexa-1,4-dienyl)butanamide;
2-hydroxy-N-(4-hydroxyphenethyl)-2-methyl-4-(2,4,5-trimethyl-3,6-dioxocyclohexa-1,4-dienyl)butanamide;
N-(3-(dimethylamino)propyl)-2-hydroxy-2-methyl-4-(2,4,5-trimethyl-3,6-dioxocyclohexa-1,4-dienyl)butanamide;
2-(4-(4-acetylpiperazin-1-yl)-3-hydroxy-3-methyl-4-oxobutyl)-3,5,6-trimethylcyclohexa-2,5-diene-1,4-dione;
2-(4-(azepan-1-yl)-3-hydroxy-3-methyl-4-oxobutyl)-3,5,6-trimethylcyclohexa-2,5-diene-1,4-dione;
2-(3-hydroxy-3-methyl-4-oxo-4-(piperazin-1-yl)butyl)-3,5,6-trimethylcyclohexa-2,5-diene-1,4-dione;
2-(4-(4-fluoropiperidin-1-yl)-3-hydroxy-3-methyl-4-oxobutyl)-3,5,6-trimethylcyclohexa-2,5-diene-1,4-dione;
2-(4-(4,4-difluoropiperidin-1-yl)-3-hydroxy-3-methyl-4-oxobutyl)-3,5,6-trimethylcyclohexa-2,5-diene-1,4-dione;
2-(4-(4-benzoylpiperazin-1-yl)-3-hydroxy-3-methyl-4-oxobutyl)-3,5,6-trimethylcyclohexa-2,5-diene-1,4-dione;
tert-butyl 4-(2-hydroxy-2-methyl-4-(2,4,5-trimethyl-3,6-dioxocyclohexa-1,4-dienyl)butanoyl)piperazine-1-carboxylate;
N-(2-fluorophenethyl)-2-hydroxy-2-methyl-4-(2,4,5-trimethyl-3,6-dioxocyclohexa-1,4-dienyl)butanamide;
N-(3-fluorophenethyl)-2-hydroxy-2-methyl-4-(2,4,5-trimethyl-3,6-dioxocyclohexa-1,4-dienyl)butanamide;
N-(4-fluorophenethyl)-2-hydroxy-2-methyl-4-(2,4,5-trimethyl-3,6-dioxocyclohexa-1,4-dienyl)butanamide N-(2-chlorophenethyl)-2-hydroxy-2-methyl-4-(2,4,5-trimethyl-3,6-dioxocyclohexa-1,4-dienyl)butanamide;
2-hydroxy-N-(4-methoxyphenyl)-2-methyl-4-(2,4,5-trimethyl-3,6-dioxocyclohexa-1,4-dienyl)butanamide;
N-(4-fluorophenyl)-2-hydroxy-2-methyl-4-(2,4,5-trimethyl-3,6-dioxocyclohexa-1,4-dienyl)butanamide;
N-(4-chlorophenyl)-2-hydroxy-2-methyl-4-(2,4,5-trimethyl-3,6-dioxocyclohexa-1,4-dienyl)butanamide;
N-(2-fluorobenzyl)-2-hydroxy-2-methyl-4-(2,4,5-trimethyl-3,6-dioxocyclohexa-1,4-dienyl)butanamide;
N-(3-fluorobenzyl)-2-hydroxy-2-methyl-4-(2,4,5-trimethyl-3,6-dioxocyclohexa-1,4-dienyl)butanamide;
N-(4-fluorobenzyl)-2-hydroxy-2-methyl-4-(2,4,5-trimethyl-3,6-dioxocyclohexa-1,4-dienyl)butanamide;

N-(2-chlorobenzyl)-2-hydroxy-2-methyl-4-(2,4,5-trimethyl-3,6-dioxocyclohexa-1,4-dienyl)butanamide;
N-(3-chlorobenzyl)-2-hydroxy-2-methyl-4-(2,4,5-trimethyl-3,6-dioxocyclohexa-1,4-dienyl)butanamide;
N-(4-chlorobenzyl)-2-hydroxy-2-methyl-4-(2,4,5-trimethyl-3,6-dioxocyclohexa-1,4-dienyl)butanamide;
2-(3-hydroxy-3-methylbutyl)-5,6-dimethyl-3-phenethylcyclohexa-2,5-diene-1,4-dione;
2-benzyl-3-(3-hydroxy-3-methylbutyl)-5,6-dimethylcyclohexa-2,5-diene-1,4-dione;
2-(3-hydroxy-3-methylbutyl)-5,6-dimethyl-3-(3-phenylpropyl)cyclohexa-2,5-diene-1,4-dione;
2-(3-hydroxy-3-methylbutyl)-5,6-dimethyl-3-(4-(trifluoromethyl)phenyl)cyclohexa-2,5-diene-1,4-dione;
2-(3-hydroxy-3-methylbutyl)-5,6-dimethyl-3-(naphthalen-2-yl)cyclohexa-2,5-diene-1,4-dione;
2-(benzofuran-2-yl)-3-(3-hydroxy-3-methylbutyl)-5,6-dimethylcyclohexa-2,5-diene-1,4-dione;
2-(4-chlorophenyl)-3-(3-hydroxy-3-methylbutyl)-5,6-dimethylcyclohexa-2,5-diene-1,4-dione;
2-(4-ethylphenyl)-3-(3-hydroxy-3-methylbutyl)-5,6-dimethylcyclohexa-2,5-diene-1,4-dione;
2-(3-hydroxy-3-methylbutyl)-5,6-dimethyl-3-(3-(trifluoromethyl)phenyl)cyclohexa-2,5-diene-1,4-dione;
2-(4-tert-butylphenyl)-3-(3-hydroxy-3-methylbutyl)-5,6-dimethylcyclohexa-2,5-diene-1,4-dione;
2-(4-fluorophenyl)-3-(3-hydroxy-3-methylbutyl)-5,6-dimethylcyclohexa-2,5-diene-1,4-dione;
2-(3-fluorophenyl)-3-(3-hydroxy-3-methylbutyl)-5,6-dimethylcyclohexa-2,5-diene-1,4-dione;
2-(3-hydroxy-3-methylbutyl)-3,5-dimethyl-6-(4-(trifluoromethyl)phenyl)cyclohexa-2,5-diene-1,4-dione;
2-(3-hydroxy-3-methylbutyl)-6-(4-methoxyphenyl)-3,5-dimethylcyclohexa-2,5-diene-1,4-dione;
2-(3,4-difluorophenyl)-6-(3-hydroxy-3-methylbutyl)-3,5-dimethylcyclohexa-2,5-diene-1,4-dione;
2-(4-fluorophenyl)-6-(3-hydroxy-3-methylbutyl)-3,5-dimethylcyclohexa-2,5-diene-1,4-dione;
2-(3-hydroxy-3-methylbutyl)-3-(4-methoxyphenyl)-5,6-dimethylcyclohexa-2,5-diene-1,4-dione;
2-(3,5-bis(trifluoromethyl)phenyl)-3-(3-hydroxy-3-methylbutyl)-5,6-dimethylcyclohexa-2,5-diene-1,4-dione;
2-(4-chlorophenyl)-6-(3-hydroxy-3-methylbutyl)-3,5-dimethylcyclohexa-2,5-diene-1,4-dione;
and all stereoisomers, mixtures of stereoisomers, prodrugs, metabolites, salts, phosphate substituted forms, crystalline forms, non-crystalline forms, deuterated forms, hydrates and solvates thereof.

For all the formulations and methods described herein, any composition in the quinone form can also be used in its reduced form (hydroquinone) when desired. That is, the compounds recited herein as cyclohexadienedione compounds (oxidized quinone) form can also be used in their benzenediol (reduced hydroquinone) form as desired.

While the compounds described herein can occur and can be used as the neutral (non-salt) compound, the description is intended to embrace all salts of the compounds described herein, as well as methods of using such salts of the compounds. In one embodiment, the salts of the compounds comprise pharmaceutically acceptable salts. Pharmaceutically acceptable salts are those salts which can be administered as drugs or pharmaceuticals to humans and/or animals and which, upon administration, retain at least some of the biological activity of the free compound (neutral compound or non-salt compound). The desired salt of a basic compound may be prepared by methods known to those of skill in the art by treating the compound with an acid. Examples of inorganic acids include, but are not limited to, hydrochloric acid, hydrobromic acid, sulfuric acid, nitric acid, and phosphoric acid. Examples of organic acids include, but are not limited to, formic acid, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, sulfonic acids, and salicylic acid. Salts of basic compounds with amino acids, such as aspartate salts and glutamate salts, can also be prepared. The desired salt of an acidic compound can be prepared by methods known to those of skill in the art by treating the compound with a base. Examples of inorganic salts of acid compounds include, but are not limited to, alkali metal and alkaline earth salts, such as sodium salts, potassium salts, magnesium salts, and calcium salts; ammonium salts; and aluminum salts. Examples of organic salts of acid compounds include, but are not limited to, procaine, dibenzylamine, N-ethylpiperidine, N,N-dibenzylethylenediamine, and triethylamine salts. Salts of acidic compounds with amino acids, such as lysine salts, can also be prepared.

The invention also includes all stereoisomers of the compounds, including diastereomers and enantiomers. The invention also includes mixtures of stereoisomers in any ratio, including, but not limited to, racemic mixtures. Unless stereochemistry is explicitly indicated in a structure, the structure is intended to embrace all possible stereoisomers of the compound depicted. If stereochemistry is explicitly indicated for one portion or portions of a molecule, but not for another portion or portions of a molecule, the structure is intended to embrace all possible stereoisomers for the portion or portions where stereochemistry is not explicitly indicated.

The compounds can be administered in prodrug form. Prodrugs are derivatives of the compounds, which are themselves relatively inactive but which convert into the active compound when introduced into the subject in which they are used by a chemical or biological process in vivo, such as an enzymatic conversion. Suitable prodrug formulations include, but are not limited to, peptide conjugates of the compounds of the invention and esters of compounds of the inventions. Further discussion of suitable prodrugs is provided in H. Bundgaard, Design of Prodrugs, New York: Elsevier, 1985; in R. Silverman, The Organic Chemistry of Drug Design and Drug Action, Boston: Elsevier, 2004; in R. L. Juliano (ed.), Biological Approaches to the Controlled Delivery of Drugs (Annals of the New York Academy of Sciences, v. 507), New York: New York Academy of Sciences, 1987; and in E. B. Roche (ed.), Design of Biopharmaceutical Properties Through Prodrugs and Analogs (Symposium sponsored by Medicinal Chemistry Section, APhA Academy of Pharmaceutical Sciences, November 1976 national meeting, Orlando, Fla.), Washington: The Academy, 1977.

Metabolites of the compounds are also embraced by the invention.

"$C_1$-$C_6$ alkyl" is intended to embrace a saturated linear, branched, cyclic, or a combination thereof, hydrocarbon of 1 to 6 carbon atoms. Examples of "$C_1$-$C_6$ alkyl" are methyl, ethyl, n-propyl, isopropyl, cyclopropyl, n-butyl, isobutyl, sec-butyl, t-butyl, cyclobutyl, cyclopropyl-methyl, methylcyclopropyl, pentyl (where the point of attachment of the pentyl group to the remainder of the molecule can be at any location on the pentyl fragment), cyclopentyl, hexyl (where the point of attachment of the hexyl group to the remainder of the molecule can be at any location on the hexyl fragment), and cyclohexyl.

The terms "($C_0$-$C_4$)-alkyl" "($C_0$-$C_6$)-alkyl" "($C_0$-$C_8$)-alkyl" are intended to embrace a saturated linear, branched, cyclic, or a combination of linear and/or branched and/or cyclic hydrocarbon chain and/or ring of 1 to 4, 1 to 6, or 1 to 8 carbon atoms, respectively, or, for the option of $C_0$, where the alkyl group is absent. If the absence of the alkyl group results in an open valence, as in —C(=O)—$C_0$ alkyl, then $C_0$ alkyl represents a hydrogen atom. This term can represent either a monovalent or a divalent hydrocarbon chain, for example, ($C_0$-$C_8$)-alkyl can embrace ($C_1$-$C_8$)-alkyl and ($C_1$-$C_8$)-alkylene chains. Terms such as "($C_0$-$C_8$)-haloalkyl" are interpreted in a similar manner, that is, as $C_1$-$C_8$ haloalkyl or as an absent group, where if the absent group results in an open valence, as in —C(=O)—$C_0$ haloalkyl, then $C_0$ alkyl represents a hydrogen atom.

"$C_1$-$C_6$ alkylene" is intended to embrace a divalent saturated linear, or branched, hydrocarbon chain of 1 to 6 carbon atoms. Examples of "$C_1$-$C_6$ alkylene" are, but are not limited to, —$CH_2$—, —$(CH_2)_2$—, —$CH(CH_3)$—, —$C(CH_3)_2$—, —$(CH_2)_3$—, —$CH_2$—$CH(CH_3)$—$CH_2$—, —$CH_2$—$C(CH_3)_2$—$CH_2$—, —$CH_2$—$CH_2$—$CH(CH_3)$—, —$CH_2$—$CH_2$—$C(CH_3)_2$—, —$(CH_2)_4$—, —$(CH_2)_5$—, —$(CH_2)_6$—.

"Halogen" or "halo" designates fluoro, chloro, bromo, and iodo.

"$C_1$-$C_6$ haloalkyl" is intended to embrace any $C_1$-$C_6$ alkyl substituent having at least one halogen substituent; the halogen can be attached via any valence on the $C_1$-$C_6$ alkyl group. Some examples of $C_1$-$C_6$ haloalkyl is —$CF_3$, —$CCl_3$, —$CHF_2$, —$CHCl_2$, —$CHBr_2$, —$CH_2F$, —$CH_2Cl$.

The term "aryl" is intended to embrace an aromatic cyclic hydrocarbon group of from 6 to 20 carbon atoms having a single ring (e.g., phenyl) or multiple condensed (fused) rings (e.g., naphthyl or anthryl). A preferred aryl group is $C_6$-$C_{10}$ aryl.

The terms "heterocycle", "heterocyclic", "heterocyclo", and "heterocyclyl" are intended to encompass a monovalent, saturated, or partially unsaturated, carbocyclic radical having one or more rings incorporating one, two, three or four heteroatoms within the ring (chosen from nitrogen, oxygen, and/or sulfur). Preferably the heterocyclic ring has between 2 and 6 carbon atoms. Examples of heterocycles include morpholine, piperidine, piperazine, thiazolidine, pyrazolidine, pyrazoline, imidazolidine, pyrrolidine, tetrahydropyran, tetrahydrofuran, quinuclidine, and the like.

The terms "heteroaryl", is intended to encompass a monovalent aromatic, carbocyclic radical having one or more rings incorporating one, two, three or four heteroatoms within the ring (chosen from nitrogen, oxygen, and/or sulfur). Preferably the heteroaryl ring has between 2 and 6 carbon atoms. Examples of heteroaryl include pyridine, pyrazine, imidazoline, thiazole, isothiazole, pyrazine, triazine, pyrimidine, pyridazine, pyrazole, thiophene, pyrrole, pyran, furan, indole, quinoline, quinazoline, benzimidazole, benzothiophene, benzofuran, benzoxazole, benzothiazole, benzotriazole, imidazo-pyridines, pyrazolo-pyridines, pyrazolo-pyrazine, acridine, carbazole, and the like.

The substituent "oxo" is =O, that is, an oxygen with a double bond to the atom to which it is attached. When oxo is listed as a potential substituent, it is intended to be a substituent only on atoms within groups where such substitution is chemically possible. For example, if a list of substituents for cyclohexyl and benzene groups recites "oxo" among the possibilities, the oxo group would only be available for substitution on the cycloalkyl group, and not on the benzene group, where such a substitution would exceed the valence of any carbon atom of the benzene group. Similarly, the oxo group would not be bonded to either of the two sp-hybridized carbons involved in an alkyne group.

Diseases Amenable to Treatment or Suppression with Compounds and Methods of the Invention A variety of diseases are believed to be caused or aggravated by oxidative stress affecting normal electron flow in the cells or caused by reactive oxygen species. Diseases caused by energy impairment include, but are not limited to, i) diseases due to deprivation, poisoning or toxicity of oxygen, and qualitative or quantitative disruption in the transport of oxygen such as hemoglobinopathies, for example thalassemia or sickle cell anemia; ii) diseases induced by contrast agents which include nephropathy, such as contrast induced nephropathy (CIN); and iii) damage due to radiation exposure or injury.

Assessment and Efficacy of Therapy

The compounds of the invention can be used in biochemical tests or assays. Such tests can include incubation of one or more compounds of the invention with a tissue or cell sample from a subject to evaluate a subject's potential response (or the response of a specific subset of subjects) to administration of said one or more compounds, or to determine which compound of the invention produces the optimum effect in a specific subject or subset of subjects.

In vitro assessment of whether a redox-active compound of the invention is capable of treating a patient afflicted with sickle cell disease may also be achieved by subjecting a sample of blood cells from a patient afflicted with sickle cell to conditions such that the blood cells in the sample will sickle, and comparing the amount of sickling of the blood cells in the presence of the redox-active therapeutic with the amount of sickling of the cells in the absence of the redox-active therapeutic, wherein an absence of sickling or a reduction in the amount of sickling in the blood cells in the presence of the redox-active therapeutic compared with the amount of sickling of the blood cells in the absence of the redox-active therapeutic indicates that the redox-active therapeutic may be capable of treating a subject afflicted with sickle cell disease.

Additionally the efficacy of the redox-active therapeutic of the invention in treating a patient afflicted with sickle cell disease can also be determined by its ability to inhibit polymerization of hemoglobin. A suitable sample of hemoglobin from a subject afflicted with sickle cell disease can be subjected to conditions such that the hemoglobin polymerizes; and the amount of turbidity of the sample is compared in the presence of the redox-active therapeutic with the amount of turbidity of the sample in the absence of the redox-active therapeutic, wherein an absence or reduction in the amount of turbidity in the sample in the presence of the redox-active compound agent compared with the amount of turbidity in the sample in the absence of the redox-active therapeutic indicates that the redox active agent is capable of inhibiting polymerization of hemoglobin. One skilled in the art would know under what conditions hemoglobin polymerizes. One example is the condition wherein oxygen tension is reduced. One skilled in the art would know methods to use to compare the amount of sickling in samples. One example is a visual comparison. Such visual comparison may be done in several ways including but not limited to under a microscope and with the naked eye. One skilled in the art would know methods to use to compare the turbidity in samples. One example is the use of a spectrophotometer. As used herein, "turbidity" includes the opacity caused by suspended particles or cells in a solution wherein a higher turbidity indicates that the sample has more polymerization or aggregation than a sample with lower turbidity.

An assessment of whether a redox-active therapeutic of the invention is capable of treating a patient afflicted with radio contrast neuropathy can be achieved by measuring increase in serum creatine levels or decrease in renal blood flow.

An increase in serum creatine level as a measurable physiological parameter defines a contrast induced nephropathy condition, as understood by the skilled artisan. An increase in serum creatine levels of between about 25% to about 70%, or even higher, from reference values defines contrast induced nephropathy, such as an increase within the range of about 25% to about 50% in serum creatinine levels. Examples of reference values are between about 0.8 mg/dl and about 1.4 mg/dl in adult males, between about 0.6 mg/dl and about 1.1 mg/dl in adult females, and between about 0.2 mg/dl and about 1.0 mg/dl in children (see World-Wide-Web.rnceus.com/renal/renalcreat.html). In a further embodiment, an increase of about 25, about 30, about 35, about 40, about 45, about 50, about 55, about 60, about 65 and about 70%, and every range which lies in any ranges defined by two of the before mentioned values, where the lower limit of said range is defined by the lower value and the upper limit of said range by the higher value, e.g. a range of about 25% to about 30%, about 25% to about 35%, about 30% to about 60%, etc., can be indicative of contrast induced nephropathy.

A decrease in renal blood flow induced by contrast media is another measurable hemodynamic parameter which defines a disease condition as understood by the skilled artisan. Reference value for blood flow in the kidney is approximately 20% of the cardiac output per minute, and thus lies at about 1000 ml/min in a healthy human. A range of a decrease in renal blood flow, of between about a 20% decrease and about an 80% or even larger decrease in renal blood flow from reference values, defines contrast induced nephropathy. In a further embodiment, a decrease of about 20, about 25, about 30, about 35, about 40, about 45, about 50, about 55, about 60, about 65, about 70, about 75, about 80, about 85 and about 90%, and every value or value range which lies in any range defined by two of the beforementioned values, where the lower limit of said range is defined by the lower value and the upper limit of said range by the higher value, e.g. a range of about 25% to about 30%, about 20% to about 35%, about 30% to about 60%, etc., can be indicative of contrast induced nephropathy. The renal blood flow can be measured using MRI (magnetic resonance imaging) techniques to determine renal blood flow and renal vascular resistance as well as by PAH (para-amino hippuric acid) infusion techniques.

The utility of the redox-active therapeutic compounds of the present invention may be demonstrated as radioprotective agents both in vitro and in vivo. For example, the ability of cultured cells to form clones (colonies) may be evaluated as a function of exposure to X-ray dose. Cells are either not treated or are treated with a redox-active therapeutic 30 minutes prior to exposure. The degree of retention of ability to form clones after exposure, in comparison to untreated cells, is directly related to the protective effect of the drug. A typical experiment of this type may be carried out essentially as described by Snyder and Lachmann Radiation Res. (1989) 120:121-128.

Alternatively, the utility of the redox-active therapeutic compound as radioprotective agent can be evaluated by measuring the production of DNA strand breaks upon exposure to X-ray dose. Cells are either not drug treated or are treated with a test agent about 30 minutes prior to exposure. The extent of DNA strand breakage after exposure, in comparison to that in untreated cells, is inversely related to the protective effect of the drug. A typical experiment of this type may be carried out essentially as described by Snyder Int. J. Radiat. Biol. (1989) 55:773.

In vivo, the radioprotective protective properties of the redox-active therapeutic compounds of the invention may be evaluated by the survivability of mice exposed to whole body irradiation. Animals, either pre-treated with a redox-active therapeutic or untreated, are exposed to whole body irradiation (1500 rads). Untreated control animals are expected to survive about 12-15 days. The degree of survivability of the treated animals, in comparison to the untreated controls, is directly related to the protective effect of the redox-active therapeutic treatment. A typical experiment of this type may be carried out essentially as described by Carroll et al. J. Med. Chem. (1990) 33:2501.

Additionally, the production of DNA strand breaks in lymphocytes taken from treated animals exposed to whole body irradiation may be evaluated in comparison to untreated control animals. Alternatively, the viability and clonogenicity of bone marrow cells taken from treated animals exposed to whole body irradiation may be evaluated in comparison to cells taken from untreated control animals as described by Pike and Robinson J. Cell Physiol. (1970) 76:77-84.

Pharmaceutical Formulations

The compounds described herein can be formulated as pharmaceutical compositions by formulation with additives such as pharmaceutically acceptable excipients, pharmaceutically acceptable carriers, and pharmaceutically acceptable vehicles. Suitable pharmaceutically acceptable excipients, carriers and vehicles include processing agents and drug delivery modifiers and enhancers, such as, for example, calcium phosphate, magnesium stearate, talc, monosaccharides, disaccharides, starch, gelatin, cellulose, methyl cellulose, sodium carboxymethyl cellulose, dextrose, hydroxypropyl-β-cyclodextrin, polyvinylpyrrolidone, low melting waxes, ion exchange resins, and the like, as well as combinations of any two or more thereof. Other suitable pharmaceutically acceptable excipients are described in "Remington's Pharmaceutical Sciences," Mack Pub. Co., New Jersey (1991), and "Remington: The Science and Practice of Pharmacy," Lippincott Williams & Wilkins, Philadelphia, 20th edition (2003) and 21st edition (2005), incorporated herein by reference.

A pharmaceutical composition can comprise a unit dose formulation, where the unit dose is a dose sufficient to have a therapeutic or suppressive effect.

Pharmaceutical compositions containing the compounds of the invention may be in any form suitable for the intended method of administration, including, for example, a solution, a suspension, or an emulsion. Liquid carriers are typically used in preparing solutions, suspensions, and emulsions. Liquid carriers contemplated for use in the practice of the present invention include, for example, water, saline, pharmaceutically acceptable organic solvent(s), pharmaceutically acceptable oils or fats, and the like, as well as mixtures of two or more thereof. The liquid carrier may contain other suitable pharmaceutically acceptable additives such as solubilizers, emulsifiers, nutrients, buffers, preservatives, suspending agents, thickening agents, viscosity regulators, stabilizers, and the like. Suitable organic solvents include, for example, monohydric alcohols, such as ethanol, and polyhydric alcohols, such as glycols. Suitable oils include, for example, soybean oil, coconut oil, olive oil, safflower oil, cottonseed oil, and the like. For parenteral administration, the carrier can also be an oily ester such as ethyl oleate, isopropyl myristate, and the like. Compositions of the present invention may also be in the form of microparticles, microcapsules, liposomal encapsulates, and the like, as well as combinations of any two or more thereof.

Time-release or controlled release delivery systems may be used, such as a diffusion controlled matrix system or an erodible system, as described for example in: Lee, "Diffusion-Controlled Matrix Systems", pp. 155-198 and Ron and Langer, "Erodible Systems", pp. 199-224, in "Treatise on Controlled Drug Delivery", A. Kydonieus Ed., Marcel Dekker, Inc., New York 1992. The matrix may be, for example, a biodegradable material that can degrade spontaneously in situ and in vivo for, example, by hydrolysis or enzymatic cleavage, e.g., by proteases. The delivery system may be, for example, a naturally occurring or synthetic polymer or copolymer, for example in the form of a hydrogel. Exemplary polymers with cleavable linkages include polyesters, polyorthoesters, polyanhydrides, polysaccharides, poly(phosphoesters), polyamides, polyurethanes, poly(imidocarbonates) and poly(phosphazenes).

The compounds of the invention may be administered enterally, orally, parenterally, sublingually, by inhalation (e.g. as mists or sprays), rectally, or topically in dosage unit formulations containing conventional nontoxic pharmaceutically acceptable carriers, adjuvants, and vehicles as desired. For example, suitable modes of administration include oral, subcutaneous, transdermal, transmucosal, iontophoretic, intravenous, intraarterial, intramuscular, intraperitoneal, intranasal (e.g. via nasal mucosa), subdural, rectal, gastrointestinal, and the like, and directly to a specific or affected organ or tissue. For delivery to the central nervous system, spinal and epidural administration, or administration to cerebral ventricles, can be used. Topical administration may also involve the use of transdermal administration such as transdermal patches or iontophoresis devices. The term parenteral as used herein includes subcutaneous, intravenous, intramuscular, and intrasternal injection or infusion techniques. The compounds are mixed with pharmaceutically acceptable carriers, adjuvants, and vehicles appropriate for the desired route of administration. Oral administration is a preferred route of administration, and formulations suitable for oral administration are preferred formulations. The compounds described for use herein can be administered in solid form, in liquid form, in aerosol form, or in the form of tablets, pills, powder mixtures, capsules, granules, injectables, creams, solutions, suppositories, enemas, colonic irrigations, emulsions, dispersions, food premixes, and in other suitable forms. The compounds can also be administered in liposome formulations. The compounds can also be administered as prodrugs, where the prodrug undergoes transformation in the treated subject to a form which is therapeutically effective. Additional methods of administration are known in the art.

Injectable preparations, for example, sterile injectable aqueous or oleaginous suspensions, may be formulated according to the known art using suitable dispersing or wetting agents and suspending agents. The sterile injectable preparation may also be a sterile injectable solution or suspension in a nontoxic parenterally acceptable diluent or solvent, for example, as a solution in propylene glycol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Solid dosage forms for oral administration may include capsules, tablets, pills, powders, and granules. In such solid dosage forms, the active compound may be admixed with at least one inert diluent such as sucrose, lactose, or starch. Such dosage forms may also comprise additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, cyclodextrins, and sweetening, flavoring, and perfuming agents.

The compounds of the present invention can also be administered in the form of liposomes. As is known in the art, liposomes are generally derived from phospholipids or other lipid substances. Liposomes are formed by mono- or multilamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and phosphatidyl cholines (lecithins), both natural and synthetic. Methods to form liposomes are known in the art. See, for example, Prescott, Ed., *Methods in Cell Biology*, Volume XIV, Academic Press, New York, N.W., p. 33 et seq. (1976).

The compounds of the present invention can also be administered in a formulation comprising a first and second compound wherein the first compound is effective against an oxidative stress disorder and the second compound is one or more compounds of the present invention. The formulation of the present invention may comprise two or more redox-therapeutics as described herein.

The invention also provides articles of manufacture and kits containing materials useful for treating or suppressing oxidative stress diseases. The invention also provides kits comprising any one or more of the compounds of the invention.

In other aspects, the kits may be used for any of the methods described herein, including, for example, to treat an individual with an oxidative stress disorder, or to suppress an oxidative stress disorder in an individual.

The amount of active ingredient that may be combined with the carrier materials to produce a single dosage form will vary depending upon the host to which the active ingredient is administered and the particular mode of administration. It will be understood, however, that the specific dose level for any particular patient will depend upon a variety of factors including the activity of the specific compound employed, the age, body weight, body area, body mass index (BMI), general health, sex, and diet of the patient; time of administration, route of administration, rate of excretion, or drug combination; and the type, progression, and severity of the particular disease undergoing therapy. The pharmaceutical unit dosage chosen is usually fabricated and administered to provide a defined final concentration of drug in the blood, tissues, organs, or other targeted region of the body. The therapeutically effective amount or effective amount for a given situation can be readily determined by routine experimentation and is within the skill and judgment of the ordinary clinician.

Examples of dosages which can be used are an effective amount within the dosage range of about 0.1 mg/kg to about 300 mg/kg body weight, or within about 1.0 mg/kg to about 100 mg/kg body weight, or within about 1.0 mg/kg to about 50 mg/kg body weight, or within about 1.0 mg/kg to about 30 mg/kg body weight, or within about 1.0 mg/kg to about 10 mg/kg body weight, or within about 10 mg/kg to about 100 mg/kg body weight, or within about 50 mg/kg to about 150 mg/kg body weight, or within about 100 mg/kg to about 200 mg/kg body weight, or within about 150 mg/kg to about 250 mg/kg body weight, or within about 200 mg/kg to about 300 mg/kg body weight, or within about 250 mg/kg to about 300 mg/kg body weight. Compounds of the present invention may be administered in a single daily dose, or the total daily dosage may be administered in divided dosage of two, three or four times daily.

While the compounds of the invention can be administered as the sole active pharmaceutical agent, they can also be used in combination with one or more other agents used in the treatment or suppression of disorders.

When additional active agents are used in combination with the compounds of the present invention, the additional active agents may generally be employed in therapeutic amounts as indicated in the Physicians' Desk Reference (PDR) 53rd Edition (1999), or such therapeutically useful amounts as would be known to one of ordinary skill in the art.

The compounds of the invention and the other therapeutically active agents can be administered at the recommended maximum clinical dosage or at lower doses. Dosage levels of the active compounds in the compositions of the invention may be varied so as to obtain a desired therapeutic response depending on the route of administration, severity of the disease and the response of the patient. When administered in combination with other therapeutic agents, the therapeutic agents can be formulated as separate compositions that are given at the same time or different times, or the therapeutic agents can be given as a single composition.

Preparation of Compounds of the Invention

In general, the nomenclature used in this Application was generated with the help of naming package within the ChemOffice® version 11.0 suite of programs by Cambridge-Soft Corp (Cambridge, Mass.).

The compounds of this invention can be prepared from readily available starting materials using general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Preparation of the redox-active therapeutics of this invention is provided in co-assigned US Patent Application Publications No. 2006/0281809, 2007/0072943, 2007/0225261, 2009/0118257 and International Patent Publication No. WO 2009/089224.

Furthermore, the compounds of this invention will typically contain one or more chiral centers. Accordingly, if desired, such compounds can be prepared or isolated as pure stereoisomers, i.e., as individual enantiomers or diastereomers, or as stereoisomer-enriched mixtures. All such stereoisomers (and enriched mixtures) are included within the scope of this invention, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents and the like.

The disclosures of all publications, patents, patent applications and published patent applications referred to herein by an identifying citation are hereby incorporated herein by reference in their entirety.

Although the foregoing invention has been described in some detail by way of illustration and example for purposes of clarity of understanding, it is apparent to those skilled in the art that certain minor changes and modifications will be practiced. Therefore, the description and examples should not be construed as limiting the scope of the invention.

What is claimed is:

1. A method for reducing, preventing or treating radiation injury or radiation damage in a mammal exposed to ionizing radiation, said method comprising administering to the mammal a therapeutically effective amount of alpha-tocotrienol quinone, a stereoisomer, or a mixture of stereoisomers thereof.

2. The method according to claim 1, wherein the alpha-tocotrienol quinone, or stereoisomer or mixture of stereoisomers thereof, is administered in combination with a pharmaceutically acceptable carrier.

3. The method according to claim 1, where the ionizing radiation is selected from the group consisting of a diagnostic X-ray, radiation therapy in cancer treatment, a CAT-scan, a mammogram, a radionuclide scan, an interventional radiological procedure under computed tomography or fluoroscopy guidance, a tissue-incorporated radionuclide from ingestion of contaminated food or water, and uncontrolled exposure to ionizing radiation from a nuclear weapon, a radioactive spill, or cosmic radiation.

4. The method according to claim 1, for preventing death of radiation-injured or radiation-damaged non-cancerous cells, comprising administering the alpha-tocotrienol quinone, or stereoisomer or mixture of stereoisomers thereof, to the mammal prior to an exposure to ionizing radiation.

5. The method according to claim 1, for reducing an effect of radiation on normal cells in a mammal at risk for incurring exposure to radiation, comprising administering the alpha-tocotrienol quinone, or stereoisomer or mixture of stereoisomers thereof, to the mammal prior to an exposure to ionizing radiation.

6. The method according to claim 1, for reducing an effect of radiation on normal cells in a mammal exposed to ionizing radiation, comprising administering the alpha-tocotrienol quinone, or stereoisomer or mixture of stereoisomers thereof, to the mammal subsequent to an accidental or intentional release of radioactive materials.

7. The method according to claim 1, for protecting non-cancerous cells against radiation therapy, comprising administering the alpha-tocotrienol quinone, or stereoisomer or mixture of stereoisomers thereof, to the mammal prior to an exposure to radiation therapy.

8. The method according to claim 1, where the method is a radiotherapy for treatment of cancer, comprising administering the alpha-tocotrienol quinone, or stereoisomer or mixture of stereoisomers thereof, to the mammal, and then administering to the mammal an effective amount of ionizing radiation, such that radiation injury to normal cells is decreased or eliminated.

9. The method according to claim 1, wherein the mammal is exposed to whole body ionizing irradiation.

10. The method according to claim 1, wherein the alpha-tocotrienol quinone, or stereoisomer or mixture of stereoisomers thereof, compound is administered systemically.

11. The method according to claim 1, wherein the alpha-tocotrienol quinone, or stereoisomer or mixture of stereoisomers thereof, is administered by a route selected from the group consisting of oral, subcutaneous, transdermal, transmucosal, iontophoretic, intravenous, intraarterial, intramuscular, intraperitoneal, intranasal, subdural, spinal, epidural, rectal, gastrointestinal, and combinations thereof.

12. The method according to claim 1, wherein the method comprises administering a therapeutically effective amount of alpha-tocotrienol quinone.

13. The method according to claim 12, wherein the administering is oral.

* * * * *